US010765570B2

(12) United States Patent
Weisman et al.

(10) Patent No.: US 10,765,570 B2
(45) Date of Patent: *Sep. 8, 2020

(54) ABSORBENT ARTICLES HAVING DISTRIBUTION MATERIALS

(71) Applicant: The Procter & Gamble Company, Cincinnati, OH (US)

(72) Inventors: Paul Thomas Weisman, Cincinnati, OH (US); Andrea Peri, Kronberg (DE); Kenneth Michael Hamall, West Chester, OH (US); Aniruddha Chatterjee, Kelkheim (DE); Jörg Endres, Frankfurt am Main (DE); Mattias Schmidt, Idstein (DE); Sandra Sautter, Hessen (DE); Gene Xiaoqing Huang, Mason, OH (US); Darrell Ian Brown, Mason, OH (US); Ward William Ostendorf, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1217 days.

This patent is subject to a terminal disclaimer.

(21) Appl. No.: 14/543,967

(22) Filed: Nov. 18, 2014

(65) Prior Publication Data

US 2016/0136011 A1 May 19, 2016

(51) Int. Cl.
*A61F 13/53* (2006.01)
*A61F 13/551* (2006.01)
(Continued)

(52) U.S. Cl.
CPC ........ *A61F 13/53* (2013.01); *A61F 13/53708* (2013.01); *A61F 13/55105* (2013.01);
(Continued)

(58) Field of Classification Search
CPC ........ A61F 13/51; A61F 13/53; A61F 13/532; A61F 13/5323; A61F 13/537;
(Continued)

(56) References Cited

U.S. PATENT DOCUMENTS 3,301,746 A 1/1967 Sanford et al.
3,323,983 A 6/1967 Palmer et al.
(Continued)

FOREIGN PATENT DOCUMENTS

EP 0 617 164 B1 8/1997
EP 1 876 291 A2 1/2005
(Continued)

OTHER PUBLICATIONS

US 5,972,466 A, 10/1999, Trokhan (withdrawn)
(Continued)

*Primary Examiner* — Peter S Vasat
(74) *Attorney, Agent, or Firm* — Christian M. Best

(57) ABSTRACT

An absorbent article comprises a liquid permeable topsheet, a liquid impermeable backsheet, an absorbent core positioned at least partially intermediate the topsheet and the backsheet, and a distribution material comprising a wet-laid, three-dimensional fibrous substrate comprising at least 80% pulp fibers by weight of the wet-laid, three-dimensional fibrous substrate. The wet-laid, three-dimensional fibrous substrate comprises a continuous network region and a plurality of discrete zones that are dispersed throughout the continuous network region. The continuous network region comprises a first average density and the plurality of discrete zones comprise a second average density. The discrete zones are dispersed throughout the continuous network region. The first average density and the second average density are different.

21 Claims, 19 Drawing Sheets

(51) Int. Cl.
*A61F 13/537* (2006.01)
*A61F 13/15* (2006.01)
*A61L 15/28* (2006.01)
*A61F 13/49* (2006.01)

(52) U.S. Cl.
CPC .. *A61F 13/55115* (2013.01); *A61F 13/55145* (2013.01); *A61L 15/28* (2013.01); *A61F 2013/15447* (2013.01); *A61F 2013/15487* (2013.01); *A61F 2013/49092* (2013.01); *A61F 2013/530007* (2013.01); *A61F 2013/53739* (2013.01); *A61F 2013/53778* (2013.01)

(58) Field of Classification Search
CPC ............ A61F 13/5376; A61F 13/55105; A61F 13/55115; A61F 2013/15422; A61F 2013/51038; A61F 2013/5104; A61F 2013/51054
See application file for complete search history.

(56) References Cited

U.S. PATENT DOCUMENTS

| | | | |
|---|---|---|---|
| 3,700,623 A | 10/1972 | Keim | |
| 3,772,076 A | 11/1973 | Keim | |
| 3,860,003 A | 1/1975 | Buell | |
| 3,974,025 A | 8/1976 | Ayers | |
| 3,994,771 A | 11/1976 | Morgan, Jr. et al. | |
| 4,011,389 A | 3/1977 | Langdon | |
| 4,191,609 A | 3/1980 | Trokhan | |
| 4,191,756 A | 3/1980 | Masi et al. | |
| 4,232,674 A * | 11/1980 | Melican | A61F 13/206 604/369 |
| 4,300,981 A | 11/1981 | Carstens | |
| 4,391,878 A | 7/1983 | Drach | |
| 4,440,597 A | 4/1984 | Wells et al. | |
| 4,514,345 A | 4/1985 | Johnson et al. | |
| 4,528,239 A | 7/1985 | Trokhan | |
| 4,529,480 A | 7/1985 | Trokhan | |
| 4,557,801 A | 12/1985 | Avis | |
| 4,637,859 A | 1/1987 | Trokhan | |
| 4,795,453 A | 1/1989 | Wolfe | |
| 4,935,021 A * | 6/1990 | Huffman | A61F 13/49011 604/385.26 |
| 5,059,282 A | 10/1991 | Ampulski et al. | |
| 5,059,283 A | 10/1991 | Hood et al. | |
| 5,073,235 A | 12/1991 | Trokhan | |
| 5,098,522 A | 3/1992 | Smurkoski et al. | |
| 5,151,092 A | 9/1992 | Buell et al. | |
| 5,164,046 A | 11/1992 | Ampulski et al. | |
| 5,217,445 A * | 6/1993 | Young | A61F 13/15203 604/378 |
| 5,221,274 A | 6/1993 | Buell et al. | |
| 5,221,435 A | 6/1993 | Smith, Jr. | |
| 5,245,025 A * | 9/1993 | Trokhan | D21F 11/006 536/56 |
| 5,246,545 A | 9/1993 | Ampulski et al. | |
| 5,246,546 A | 9/1993 | Ampulski | |
| 5,260,171 A | 11/1993 | Smurkoski et al. | |
| 5,275,700 A | 1/1994 | Trokhan | |
| 5,277,761 A | 1/1994 | Van Phan et al. | |
| 5,294,475 A | 3/1994 | Mcneil | |
| 5,300,054 A | 4/1994 | Feist et al. | |
| 5,328,565 A | 7/1994 | Rasch et al. | |
| 5,334,289 A | 8/1994 | Trokhan et al. | |
| 5,364,504 A | 11/1994 | Smurkoski et al. | |
| 5,366,785 A | 11/1994 | Sawdai | |
| 5,383,869 A | 1/1995 | Osborn, III | |
| 5,401,267 A | 3/1995 | Couture-Dorschner et al. | |
| 5,411,636 A | 5/1995 | Hermans et al. | |
| 5,431,786 A | 7/1995 | Rasch et al. | |
| 5,443,691 A | 8/1995 | Phan et al. | |
| 5,468,323 A | 11/1995 | Mcneil | |
| 5,496,624 A | 3/1996 | Stelljes, Jr. et al. | |
| 5,500,277 A | 3/1996 | Trokhan et al. | |
| 5,503,715 A | 4/1996 | Trokhan et al. | |
| 5,509,914 A | 4/1996 | Osborn, III | |
| 5,514,523 A | 5/1996 | Trokhan et al. | |
| 5,520,778 A | 5/1996 | Sawdai | |
| 5,527,428 A | 6/1996 | Trokhan et al. | |
| 5,529,664 A | 6/1996 | Trokhan et al. | |
| 5,534,326 A | 7/1996 | Trokhan et al. | |
| 5,549,589 A | 8/1996 | Horney et al. | |
| 5,549,790 A | 8/1996 | Van Phan | |
| 5,552,345 A | 9/1996 | Schrantz et al. | |
| 5,554,145 A | 9/1996 | Roe et al. | |
| 5,554,467 A | 9/1996 | Trokhan et al. | |
| 5,556,509 A | 9/1996 | Trokhan et al. | |
| 5,562,645 A | 10/1996 | Tanzer et al. | |
| 5,566,724 A | 10/1996 | Trokhan et al. | |
| 5,569,234 A | 10/1996 | Buell et al. | |
| 5,575,786 A | 11/1996 | Osborn, III | |
| 5,580,411 A | 12/1996 | Nease et al. | |
| 5,580,423 A * | 12/1996 | Ampulski | D32F 11/006 162/109 |
| 5,599,335 A | 2/1997 | Goldman et al. | |
| 5,609,725 A | 3/1997 | Van Phan | |
| 5,614,061 A | 3/1997 | Van Phan et al. | |
| 5,624,790 A | 4/1997 | Trokhan et al. | |
| 5,628,876 A | 5/1997 | Ayers et al. | |
| 5,629,052 A | 5/1997 | Trokhan et al. | |
| 5,637,194 A | 6/1997 | Ampulski et al. | |
| 5,654,076 A | 8/1997 | Trokhan et al. | |
| 5,656,132 A | 8/1997 | Farrington, Jr. et al. | |
| 5,665,082 A | 9/1997 | Boulanger | |
| 5,674,663 A | 10/1997 | McFarland et al. | |
| 5,679,222 A | 10/1997 | Rasch et al. | |
| 5,693,187 A | 12/1997 | Ampulski et al. | |
| 5,693,406 A | 12/1997 | Wegele et al. | |
| 5,709,775 A | 1/1998 | Trokhan et al. | |
| 5,714,041 A | 2/1998 | Ayers et al. | |
| 5,716,692 A | 2/1998 | Warner et al. | |
| 5,718,806 A | 2/1998 | Trokhan et al. | |
| 5,728,268 A | 3/1998 | Weisman et al. | |
| 5,741,402 A | 4/1998 | Trokhan et al. | |
| 5,744,007 A | 4/1998 | Trokhan et al. | |
| 5,776,307 A | 7/1998 | Ampulski et al. | |
| 5,776,311 A | 7/1998 | Trokhan et al. | |
| 5,776,312 A | 7/1998 | Trokhan et al. | |
| 5,779,860 A | 7/1998 | Hollenberg et al. | |
| 5,795,440 A | 8/1998 | Ampulski et al. | |
| 5,804,036 A | 9/1998 | Phan et al. | |
| 5,804,281 A | 9/1998 | Phan et al. | |
| 5,814,190 A | 9/1998 | Van Phan | |
| 5,817,377 A | 10/1998 | Trokhan et al. | |
| 5,820,730 A | 10/1998 | Phan et al. | |
| 5,830,558 A | 11/1998 | Barnholtz | |
| 5,832,362 A | 11/1998 | Trokhan | |
| 5,837,103 A | 11/1998 | Trokhan et al. | |
| 5,840,403 A | 11/1998 | Trokhan et al. | |
| 5,840,411 A | 11/1998 | Stelljes, Jr. et al. | |
| 5,843,279 A | 12/1998 | Phan et al. | |
| 5,846,379 A | 12/1998 | Ampulski et al. | |
| 5,855,572 A | 1/1999 | Schmidt | |
| 5,855,738 A | 1/1999 | Weisman et al. | |
| 5,855,739 A | 1/1999 | Ampulski et al. | |
| 5,858,554 A | 1/1999 | Neal et al. | |
| 5,861,082 A | 1/1999 | Ampulski et al. | |
| 5,865,950 A | 2/1999 | Vinson et al. | |
| 5,871,887 A | 2/1999 | Trokhan et al. | |
| 5,885,421 A | 3/1999 | Ensign et al. | |
| 5,893,965 A | 4/1999 | Trokhan et al. | |
| 5,895,623 A | 4/1999 | Trokhan et al. | |
| 5,897,745 A | 4/1999 | Ampulski et al. | |
| 5,900,122 A | 5/1999 | Huston | |
| 5,904,811 A | 5/1999 | Ampulski et al. | |
| 5,906,710 A | 5/1999 | Trokhan | |
| 5,906,711 A | 5/1999 | Barnholtz | |
| 5,919,556 A | 7/1999 | Barnholtz | |
| 5,935,381 A | 8/1999 | Trokhan et al. | |
| 5,938,893 A | 8/1999 | Trokhan et al. | |
| 5,942,085 A | 8/1999 | Neal et al. | |
| 5,948,210 A | 9/1999 | Huston | |

(56) References Cited

U.S. PATENT DOCUMENTS

| | | |
|---|---|---|
| 5,951,537 A | 9/1999 | Osborn, III |
| 5,954,097 A | 9/1999 | Boutilier |
| 5,962,860 A | 10/1999 | Trokhan et al. |
| 5,972,813 A | 10/1999 | Polat et al. |
| 5,980,691 A | 11/1999 | Weisman et al. |
| 6,004,306 A | 12/1999 | Robles et al. |
| 6,010,598 A | 1/2000 | Boutilier et al. |
| 6,030,690 A | 2/2000 | Mcneil et al. |
| 6,039,839 A | 3/2000 | Trokhan et al. |
| 6,048,938 A | 4/2000 | Neal et al. |
| 6,074,525 A | 6/2000 | Richards |
| 6,086,715 A | 7/2000 | Mcneil |
| 6,090,241 A | 7/2000 | Trokhan et al. |
| 6,099,781 A | 8/2000 | Ampulski |
| 6,103,062 A | 8/2000 | Ampulski et al. |
| 6,103,067 A | 8/2000 | Stelljes, Jr. et al. |
| 6,103,953 A | 8/2000 | Cree et al. |
| 6,106,670 A | 8/2000 | Weisman et al. |
| 6,110,324 A | 8/2000 | Trokhan et al. |
| 6,113,723 A | 9/2000 | Mcneil et al. |
| 6,117,270 A | 9/2000 | Trokhan |
| 6,117,525 A | 9/2000 | Trokhan et al. |
| 6,136,146 A | 10/2000 | Phan et al. |
| 6,139,686 A | 10/2000 | Trokhan et al. |
| 6,149,849 A | 11/2000 | Ampulski |
| 6,165,319 A | 12/2000 | Heath et al. |
| 6,171,447 B1 | 1/2001 | Trokhan |
| 6,187,138 B1 | 2/2001 | Neal et al. |
| 6,193,839 B1 | 2/2001 | Ampulski et al. |
| 6,193,847 B1 | 2/2001 | Trokhan |
| 6,200,419 B1 | 3/2001 | Phan |
| 6,210,644 B1 | 4/2001 | Trokhan et al. |
| 6,238,682 B1 | 5/2001 | Klofta et al. |
| 6,251,331 B1 | 6/2001 | Ampulski et al. |
| 6,258,516 B1 | 7/2001 | Trokhan et al. |
| 6,271,532 B1 | 8/2001 | Trokhan et al. |
| 6,273,996 B1 | 8/2001 | Hollenberg et al. |
| 6,287,425 B1 | 9/2001 | Richards |
| 6,287,641 B1 | 9/2001 | Ostendorf et al. |
| 6,296,862 B1 | 10/2001 | Paul et al. |
| 6,329,565 B1 | 12/2001 | Dutkiewicz et al. |
| 6,344,241 B1 | 2/2002 | Ampulski |
| 6,358,030 B1 | 3/2002 | Ampulski |
| 6,358,594 B1 | 3/2002 | Ampulski |
| 6,368,465 B1 | 4/2002 | Stelljes, Jr. et al. |
| 6,420,013 B1 | 7/2002 | Vinson et al. |
| 6,420,100 B1 | 7/2002 | Trokhan et al. |
| 6,423,186 B1 | 7/2002 | Trokhan et al. |
| 6,432,272 B1 | 8/2002 | Hollenberg et al. |
| 6,458,447 B1 | 10/2002 | Cabell et al. |
| 6,464,831 B1 | 10/2002 | Trokhan et al. |
| 6,500,307 B2 | 12/2002 | Richards |
| 6,540,880 B1 | 4/2003 | Trokhan et al. |
| 6,551,453 B2 | 4/2003 | Weisman et al. |
| 6,554,601 B2 | 4/2003 | Ampulski et al. |
| 6,561,781 B1 | 5/2003 | Ampulski |
| 6,576,090 B1 | 6/2003 | Trokhan et al. |
| 6,576,091 B1 | 6/2003 | Cabell et al. |
| 6,590,136 B1 | 7/2003 | Young et al. |
| 6,660,129 B1 | 12/2003 | Cabell et al. |
| 6,673,202 B2 | 1/2004 | Burazin et al. |
| 6,706,152 B2 | 3/2004 | Burzain et al. |
| 6,733,833 B2 | 5/2004 | Ampulski |
| 6,743,571 B1 | 6/2004 | Hill et al. |
| 6,746,570 B2 | 6/2004 | Burzain et al. |
| 6,746,766 B2 | 6/2004 | Bond et al. |
| 6,749,719 B2 | 6/2004 | Burzain et al. |
| 6,787,000 B2 | 9/2004 | Burzain et al. |
| 6,790,314 B2 | 9/2004 | Burzain et al. |
| 6,797,114 B2 | 9/2004 | Hu |
| 6,802,937 B2 | 10/2004 | Johnston et al. |
| 6,808,790 B2 | 10/2004 | Chen et al. |
| 6,821,385 B2 | 11/2004 | Burzain et al. |
| 6,821,386 B2 | 11/2004 | Weisman et al. |
| 6,860,970 B2 | 3/2005 | Ampulski |
| 6,890,872 B2 | 5/2005 | Bond et al. |
| 6,913,859 B2 | 7/2005 | Hill et al. |
| 6,946,506 B2 | 9/2005 | Bond et al. |
| 7,094,320 B1 | 8/2006 | Phan |
| 7,118,647 B2 | 10/2006 | Cabell et al. |
| 7,128,809 B2 | 10/2006 | Vinson et al. |
| 7,265,067 B1 | 9/2007 | Phan |
| 7,311,800 B2 | 12/2007 | Russell et al. |
| 7,374,638 B2 | 5/2008 | Horenziak et al. |
| 7,374,639 B2 | 5/2008 | Ampulski et al. |
| 7,419,569 B2 | 9/2008 | Hermans et al. |
| 7,494,563 B2 | 2/2009 | Edwards et al. |
| RE40,724 E | 6/2009 | Barnholtz |
| 7,744,576 B2 | 1/2010 | Busam et al. |
| 7,687,140 B2 | 3/2010 | Manifold et al. |
| 7,691,229 B2 | 4/2010 | Vinson et al. |
| 7,704,601 B2 | 4/2010 | Manifold et al. |
| 7,741,234 B2 | 6/2010 | Smith et al. |
| 7,744,723 B2 | 6/2010 | Sheehan et al. |
| 7,750,203 B2 | 7/2010 | Becker et al. |
| 7,799,411 B2 | 9/2010 | Ostendorf et al. |
| 7,807,022 B2 | 10/2010 | Hermans et al. |
| 7,811,665 B2 | 10/2010 | Manifold et al. |
| 7,851,667 B2 | 12/2010 | Becker et al. |
| 7,869,964 B2 | 1/2011 | Rosati et al. |
| 7,894,625 B2 | 2/2011 | Tompkins, IV et al. |
| 7,914,649 B2 | 3/2011 | Ostendorf et al. |
| 7,922,705 B2 | 4/2011 | Ampulski |
| 7,939,168 B2 | 5/2011 | Manifold et al. |
| 7,960,020 B2 | 6/2011 | Manifold et al. |
| 7,967,950 B2 | 6/2011 | Horenziak et al. |
| 8,025,966 B2 | 6/2011 | Manifold et al. |
| 7,989,058 B2 | 8/2011 | Manifold et al. |
| 8,034,463 B2 | 10/2011 | Leimbach et al. |
| RE42,968 E | 11/2011 | Sheehan et al. |
| 8,135,170 B2 | 3/2012 | Tompkins, IV et al. |
| 8,163,130 B2 | 4/2012 | Polat et al. |
| 8,178,196 B2 | 5/2012 | Manifold et al. |
| 8,192,836 B2 | 6/2012 | Manifold et al. |
| 8,202,605 B2 | 6/2012 | Ostendorf et al. |
| 8,211,271 B2 | 7/2012 | Polat et al. |
| 8,282,783 B2 | 10/2012 | Phan et al. |
| 8,287,693 B2 | 10/2012 | Phan et al. |
| 8,298,376 B2 | 10/2012 | Polat et al. |
| 8,313,617 B2 | 11/2012 | Polat et al. |
| 8,657,997 B2 | 2/2014 | Polat et al. |
| 9,439,815 B2 | 9/2016 | Marinelli et al. |
| 10,517,775 B2 | 12/2019 | Weisman et al. |
| 2002/0123728 A1 | 9/2002 | Graef et al. |
| 2002/0168518 A1 | 11/2002 | Bond et al. |
| 2003/0077444 A1 | 4/2003 | Bond et al. |
| 2003/0092343 A1 | 5/2003 | Bond et al. |
| 2003/0138597 A1 | 7/2003 | Ruthven et al. |
| 2003/0168912 A1 | 9/2003 | Wodrich et al. |
| 2003/0171729 A1 | 9/2003 | Kaun et al. |
| 2003/0181115 A1 | 9/2003 | Nagasuna et al. |
| 2004/0023003 A1 | 2/2004 | Basler et al. |
| 2004/0009387 A1 | 5/2004 | Vinson et al. |
| 2004/0112783 A1 | 6/2004 | Mukai et al. |
| 2004/0154767 A1 | 8/2004 | Trokhan et al. |
| 2004/0154768 A1 | 8/2004 | Trokhan et al. |
| 2004/0154769 A1 | 8/2004 | Lorenz et al. |
| 2004/0157524 A1 | 8/2004 | Polat et al. |
| 2004/0162536 A1 | 8/2004 | Becker et al. |
| 2004/0167486 A1 | 8/2004 | Busam et al. |
| 2004/0170813 A1 | 9/2004 | Digiacomantonio et al. |
| 2004/0192136 A1 | 9/2004 | Gusky et al. |
| 2004/0025887 A1 | 12/2004 | Macaig et al. |
| 2004/0261639 A1 | 12/2004 | Vaughn et al. |
| 2005/0026529 A1 | 2/2005 | Bond |
| 2005/0034828 A1 | 2/2005 | Graf et al. |
| 2005/0045293 A1 | 3/2005 | Hermans et al. |
| 2005/0067126 A1 | 3/2005 | Horenziak et al. |
| 2005/0079785 A1 | 4/2005 | Bond et al. |
| 2005/0178513 A1 | 8/2005 | Russell et al. |
| 2005/0201965 A1 | 9/2005 | Kuhlman et al. |
| 2005/0215967 A1* | 9/2005 | Toro ............ A61F 13/475 604/378 |
| 2006/0137840 A1 | 6/2006 | Burazin et al. |

(56) References Cited

U.S. PATENT DOCUMENTS

| | | |
|---|---|---|
| 2007/0156108 A1 | 7/2007 | Becker et al. |
| 2007/0167928 A1 | 7/2007 | Becker et al. |
| 2007/0179464 A1 | 8/2007 | Becker et al. |
| 2007/0232178 A1 | 10/2007 | Polat et al. |
| 2007/0250026 A1 | 10/2007 | Venturino et al. |
| 2007/0254550 A1 | 11/2007 | Hamed et al. |
| 2007/0256802 A1 | 11/2007 | Sheehan et al. |
| 2008/0041543 A1 | 2/2008 | Dyer et al. |
| 2008/0125735 A1 | 5/2008 | Busam et al. |
| 2008/0260996 A1 | 10/2008 | Heilman et al. |
| 2008/0312622 A1 | 12/2008 | Hundorf et al. |
| 2009/0043273 A1 | 2/2009 | Carlucci et al. |
| 2009/0099793 A1 | 4/2009 | Rosati et al. |
| 2009/0110998 A1 | 4/2009 | Miyachi et al. |
| 2009/0118689 A1 | 5/2009 | Lawson et al. |
| 2009/0220741 A1 | 9/2009 | Manifold et al. |
| 2009/0220769 A1 | 9/2009 | Manifold et al. |
| 2009/0287174 A1 | 11/2009 | Carlucci et al. |
| 2010/0036342 A1 | 2/2010 | Carlucci et al. |
| 2010/0051166 A1 | 3/2010 | Hundorf et al. |
| 2010/0228210 A1 | 9/2010 | Busam et al. |
| 2010/0228211 A1 | 9/2010 | Becker et al. |
| 2010/0239946 A1 | 9/2010 | Miyachi et al. |
| 2010/0294446 A1 | 11/2010 | Manifold et al. |
| 2011/0027563 A1 | 2/2011 | Manifold et al. |
| 2011/0114277 A1 | 5/2011 | Spitzer et al. |
| 2011/0125119 A1* | 5/2011 | Weismantel ......... A61F 13/537 |
| | | 604/372 |
| 2011/0137624 A1 | 6/2011 | Weisman et al. |
| 2011/0139389 A1 | 6/2011 | Phan et al. |
| 2011/0139390 A1 | 6/2011 | Phan et al. |
| 2011/0183132 A1 | 7/2011 | Manifold et al. |
| 2011/0189435 A1 | 8/2011 | Manifold et al. |
| 2011/0189436 A1 | 8/2011 | Manifold et al. |
| 2011/0189442 A1 | 8/2011 | Manifold et al. |
| 2011/0189443 A1 | 8/2011 | Manifold et al. |
| 2011/0189451 A1 | 8/2011 | Manifold et al. |
| 2011/0206913 A1 | 8/2011 | Manifold et al. |
| 2011/0207837 A1* | 8/2011 | Luckert ................ C08J 11/08 |
| | | 521/40 |
| 2011/0212299 A1 | 9/2011 | Nyangiro et al. |
| 2011/0250413 A1 | 10/2011 | Lu et al. |
| 2011/0253329 A1 | 10/2011 | Manifold et al. |
| 2011/0268932 A1 | 11/2011 | Catalan et al. |
| 2011/0305884 A1 | 12/2011 | Manifold et al. |
| 2011/0319848 A1 | 12/2011 | McKiernan et al. |
| 2012/0107568 A1 | 5/2012 | Manifold et al. |
| 2013/0018348 A1 | 1/2013 | Carlucci et al. |
| 2013/0167305 A1* | 7/2013 | Weisman ................ D04H 3/00 |
| | | 8/137 |
| 2013/0172226 A1 | 7/2013 | Dreher et al. |
| 2013/0209749 A1 | 8/2013 | Myangiro et al. |
| 2013/0226120 A1* | 8/2013 | Van De Maele ... A61F 13/5323 |
| | | 604/372 |
| 2014/0005625 A1* | 1/2014 | Wirtz ............... A61F 13/15626 |
| | | 604/372 |
| 2014/0053994 A1 | 2/2014 | Manifold et al. |
| 2014/0163503 A1 | 6/2014 | Arizti et al. |
| 2014/0163511 A1 | 6/2014 | Roe et al. |
| 2016/0074249 A1 | 3/2016 | Rosati et al. |
| 2016/0136009 A1* | 5/2016 | Weisman ............. A61F 13/532 |
| | | 604/367 |
| 2016/0136011 A1 | 5/2016 | Peri et al. |
| 2016/0136012 A1 | 5/2016 | Peri et al. |
| 2016/0136013 A1* | 5/2016 | Peri ..................... A61F 13/537 |
| | | 604/385.101 |
| 2017/0258647 A1* | 9/2017 | Orr ....................... D04H 3/011 |
| 2018/0001879 A1 | 1/2018 | Witte et al. |

FOREIGN PATENT DOCUMENTS

| | | |
|---|---|---|
| EP | 1 505 207 A2 | 2/2005 |
| EP | 0 677 612 B2 | 6/2006 |
| EP | 1447066 | 10/2008 |
| EP | 2740449 | 11/2014 |
| GB | 2319539 A | 5/1998 |
| GB | 2510665 | 8/2014 |
| JP | 2002-506888 | 3/2002 |
| WO | WO 96/33310 A1 | 10/1996 |
| WO | WO 97/17494 A1 | 5/1997 |
| WO | WO9718783 | 5/1997 |
| WO | WO 98/44194 A1 | 10/1998 |
| WO | WO 95/11652 | 3/1999 |
| WO | WO 2005/021868 A1 | 3/2005 |
| WO | WO 2005/068720 A1 | 7/2005 |
| WO | WO 2005/080683 A2 | 9/2005 |
| WO | WO 2006/060814 A2 | 6/2006 |
| WO | WO 2007/001576 A1 | 1/2007 |
| WO | WO 2007/070124 A1 | 6/2007 |
| WO | WO 2012/052172 | 4/2012 |

OTHER PUBLICATIONS

El-Hosseiny, et al., "Effect of Fiber Length and Coarseness of the Burst Strength of Paper", TAPPI Journal, vol. 82: No. 1 (Jan. 1999), pp. 202-203.

Smook, Gary A., Second Edition Handbook for Pulp & Paper Technologists, 1992, Angus Wilde Publications, Chapter 13, pp. 194-208.

All Office Actions, Responses, Claims for U.S. Appl. No. 14/543,973, dated Nov. 18, 2014.

All Office Actions, Responses, Claims for U.S. Appl. No. 14/543,984, dated Nov. 18, 2014.

International Search Report and Written Opinion PCTUS2015059363 dated Jan. 27, 2016.

All Office Actions for U.S. Appl. No. 15/453,997.

* cited by examiner

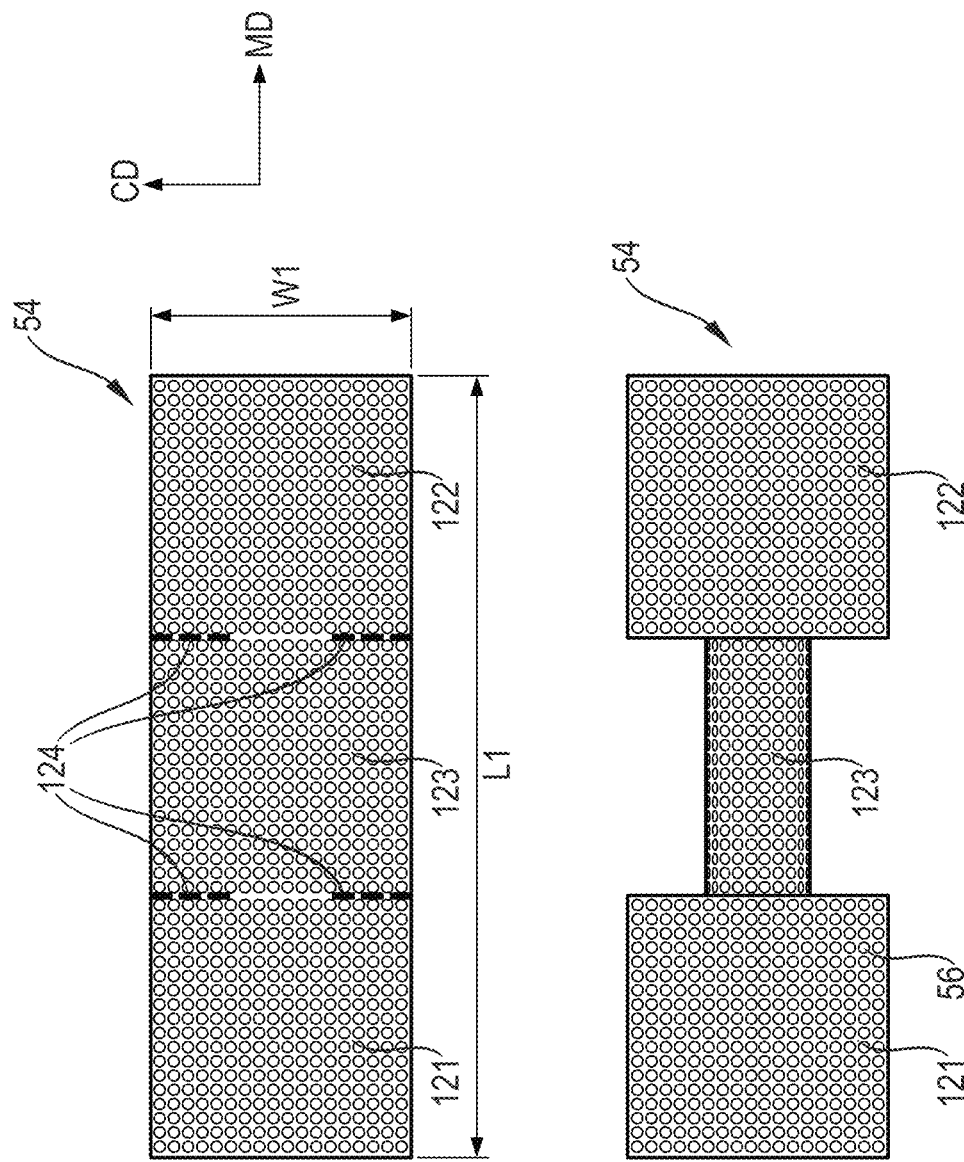

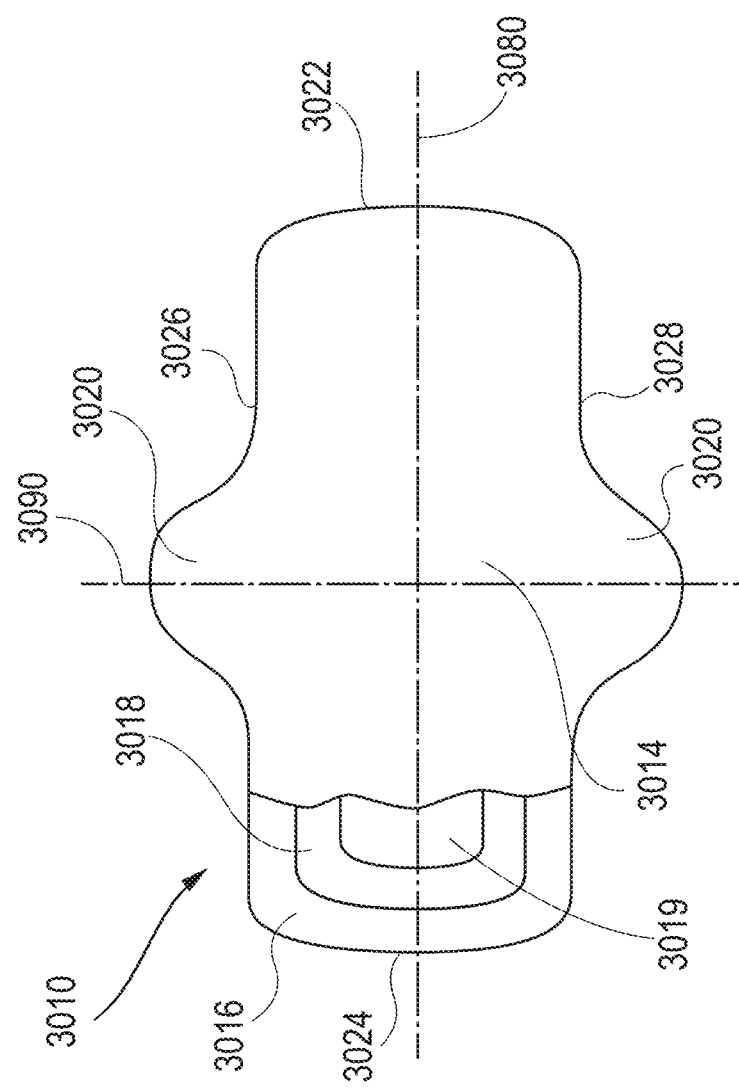

ABSORBENT ARTICLES HAVING DISTRIBUTION MATERIALS

FIELD

The present disclosure is generally directed to absorbent articles having distribution materials and, is more specifically directed to, absorbent articles having distribution materials that comprise fibrous substrates comprising pulp fibers.

BACKGROUND

Typically, absorbent articles may comprise a topsheet, a backsheet, and an absorbent core positioned at least partially intermediate the topsheet and the backsheet. The absorbent articles may comprise an acquisition layer or material and/or a distribution layer or material. The distribution material is able to receive liquid bodily exudates (i.e., menses, urine, and/or runny BM) and distribute and/or transfer them to the absorbent core, or portions thereof, in order to render the absorbent core more efficient and to distribute the liquid bodily exudates more evenly over the absorbent core. Some distribution materials are air-laid. These air-laid distribution materials at least partially collapse or lose their structure after receiving one or more insults of liquid bodily exudates. Additionally, these air-laid distribution materials, upon receiving compressive loads and/or other strains associated with wearing the absorbent article, may be subject to caliper loss and even tearing and breaking, thereby reducing their effectiveness. Therefore, there is a desire to develop distribution materials that have improved wet strength and wet integrity, and that can withstand one or more insults of liquid bodily exudates while still maintaining their structure.

SUMMARY

The present disclosure solves the problems associated with currently available air-laid distribution materials for absorbent articles by providing wet-laid and/or wet-formed distribution materials that have high wet strength and wet integrity even after receiving one or more liquid bodily exudate insults and wearer induced strains. The wet-laid or wet-formed distribution materials of the present disclosure are able to maintain their wet molded structure after wetting and wearer induced strains, thereby making them superior distribution materials. In addition, the wet-laid and/or wet-formed distribution materials of the present disclosure have the ability to maintain a three-dimensional structure after receiving one or more liquid bodily exudates insults and wearer induced strains, thereby allowing them to maintain a suitable void volume, owing to the three-dimensional structure, throughout use. Maintaining this void volume within a distribution material, as well as between layers of the distribution material, allows for better distribution of liquid bodily exudates into an absorbent core. Lastly, the wet-laid and/or wet-formed distribution materials of the present disclosure maintain their three-dimensional structure during in-use performance even after being subjected to compression packaging.

In a form, the present disclosure is directed, in part, to an absorbent article comprising a liquid permeable topsheet, a liquid impermeable backsheet, an absorbent core positioned at least partially intermediate the topsheet and the backsheet, and a distribution material comprising a wet-laid or wet-formed, three-dimensional fibrous substrate comprising at least 80% pulp fibers by weight of the wet-laid or wet-formed, three-dimensional fibrous substrate. The wet-laid or wet-formed, three-dimensional fibrous substrate comprises a continuous network region and a plurality of discrete zones that are dispersed throughout the continuous network region. The continuous network region comprises a first average density and the plurality of discrete zones comprises a second average density. The discrete zones are dispersed throughout the continuous network region. The first average density and the second average density are different.

In a form, the present disclosure is directed, in part, to an absorbent article comprising a liquid permeable topsheet, a liquid impermeable backsheet, an absorbent core positioned at least partially intermediate the topsheet and the backsheet, and a distribution material comprising a wet-laid or wet-formed, three-dimensional fibrous substrate comprising at least 80% pulp fibers by weight of the wet-laid or wet-formed, three-dimensional fibrous substrate. The wet-laid or wet-formed, three-dimensional fibrous substrate comprises a continuous network region and a plurality of discrete zones. The discrete zones are dispersed throughout the continuous network region. The continuous network region and the plurality of discrete zones have a common intensive property. The common intensive property of the continuous network region has a first value. The common intensive property of the plurality of discrete zones has a second value. The first value is different than the second value.

In a form, the present disclosure is directed, in part, to an absorbent article comprises a liquid permeable topsheet, a liquid impermeable backsheet, an absorbent core positioned at least partially intermediate the topsheet and the backsheet, and a distribution material comprising a wet-laid or wet-formed, three-dimensional fibrous substrate comprising at least 80% pulp fibers by weight of the wet-laid or wet-formed, three-dimensional fibrous substrate. The wet-laid or wet-formed, three-dimensional fibrous substrate comprises a continuous network region, a plurality of discrete zones, and a plurality of transition regions. The transition regions are positioned intermediate the continuous network region and at least some of the plurality of discrete zones.

BRIEF DESCRIPTION OF THE DRAWINGS

The above-mentioned and other features and advantages of the present disclosure, and the manner of attaining them, will become more apparent and the disclosure itself will be better understood by reference to the following description of non-limiting forms of the disclosure taken in conjunction with the accompanying drawings, wherein:

FIG. 16A is a top view of an example distribution material, or a portion thereof, comprising slits in accordance with the present disclosure;

FIG. 16B is a top view of the example distribution material of FIG. 16A comprising slits in a folded configuration that forms a "dog bone" shape in accordance with the present disclosure;

FIG. 17 is a top view of an absorbent article that is a sanitary napkin with some of the layers cut away in accordance with the present disclosure;

DETAILED DESCRIPTION

Figure 1:
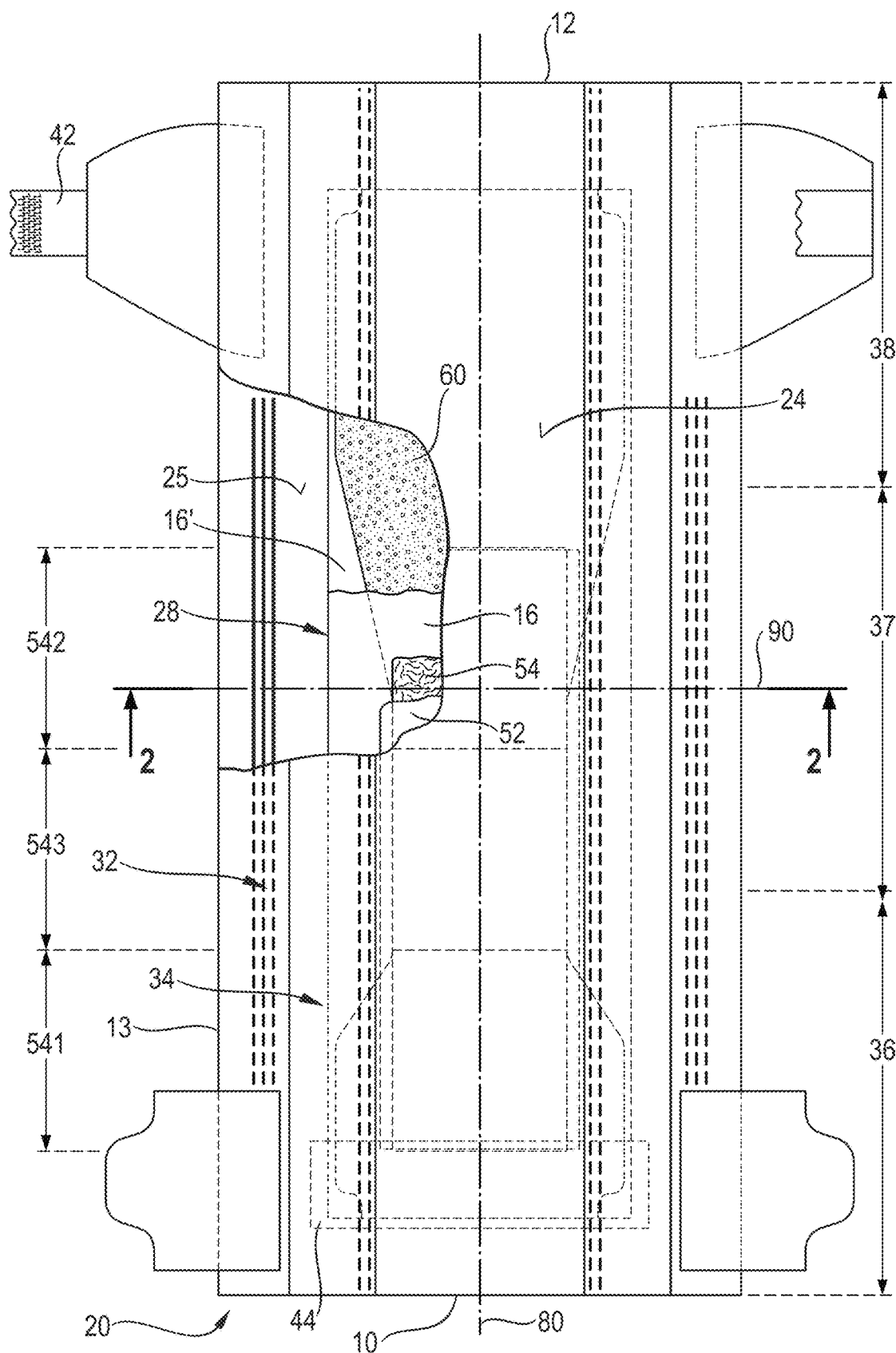
FIG. 1 is a top view of an absorbent article in the form of a diaper with some layers partially removed and comprising a distribution material in accordance with the present disclosure.

Various non-limiting forms of the present disclosure will now be described to provide an overall understanding of the principles of the structure, function, manufacture, and use of the absorbent articles having distribution materials disclosed herein. One or more examples of these non-limiting forms are illustrated in the accompanying drawings. Those of ordinary skill in the art will understand that the absorbent articles having distribution materials described herein and illustrated in the accompanying drawings are non-limiting example forms and that the scope of the various non-limiting forms of the present disclosure are defined solely by the claims. The features illustrated or described in connection with one non-limiting form may be combined with the features of other non-limiting forms. Such modifications and variations are intended to be included within the scope of the present disclosure.

DEFINITIONS

As used herein, the term "absorbent article" refers to disposable devices such as infant, child, or adult incontinence diapers, training pants, incontinence pants, sanitary napkins, and the like which are placed against or in proximity to the body of the wearer to absorb and contain the various solid and liquid bodily exudates discharged from the body (e.g., menses, runny BM, BM, and urine). Typically, these absorbent articles comprise a topsheet, backsheet, an absorbent core, optionally an acquisition system, and a distribution system, and typically other components, with the absorbent core normally placed at least partially between the topsheet and the backsheet. The absorbent articles may take on any suitable configuration.

As used herein, the term "nonwoven web" means a manufactured sheet, web, or batt of directionally or randomly orientated fibers, bonded by friction, and/or cohesion, and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers may have diameters ranging from less than about 0.001 mm to more than about 0.2 mm and may come in several different forms such as short fibers (known as staple, or chopped), continuous single fibers (filaments or monofilaments), untwisted bundles of continuous filaments (tow), and twisted bundles of continuous filaments (yarn). Nonwoven webs can be formed by many processes such as meltblowing, spunbonding, solvent spinning, electrospinning, carding, and airlaying. The basis weight of nonwoven webs is usually expressed in grams per square meter (g/m$^2$ or gsm). Bicomponent fibers, or any other suitable fibers, may also be used in forming the nonwoven webs.

As used herein, the terms "joined", "bonded", or "attached" encompass configurations wherein an element is directly secured to another element by affixing the element directly to the other element, and configurations wherein an element is indirectly secured to another element by affixing the element to intermediate member(s) which in turn are affixed to the other element.

As used herein, the term "wet-laid" is a process step in papermaking. In the wet-laid process, pulp fibers (wood or non-wood) are first mixed with chemicals and water to obtain a uniform dispersion called a slurry at very high dilutions of 0.01 percent weight to 0.5 percent weight of the fibers. The slurry is then deposited on a moving foraminous member (or wire screen) where the excess water is drained off, leaving the fibers randomly laid in a uniform substrate, which is then bonded and finished as required.

As used herein, the term "wet-formed" refers to wet-laid fibrous substrates that have a three-dimensional structure imparted to them by the papermaking process of the present disclosure.

As used herein, the term "cellulosic fiber" refers to natural fibers which typically are wood pulp fibers. Applicable wood pulps comprise chemical pulps, such as Kraft, sulfite, and sulfate pulp, as well as mechanical pulps comprising, for example, groundwood, thermomechanical pulp and chemically modified thermomechanical pulp. Pulps derived from both deciduous trees (hereinafter, also referred to as "hardwood") and coniferous trees (hereinafter, also referred to as "softwood") may be utilized. The hardwood and softwood fibers may be blended, or alternatively, may be deposited in layers to provide a stratified web.

As used herein, the term "substrate" refers to an individual, self-sustaining, integral web.

As used herein, the term "fibrous substrate" refers to an individual, self-sustaining, integral web comprising pulp fibers. The fibrous substrate may comprise two or more stratified non-self-sustaining hardwood and/or softwood portions.

As used herein, the term "layer" refers to a single self-sustaining, integral web, while the term "layers" refers to a plurality of self-sustaining, integral webs that are in a facing relationship with each other and that may be joined to each other.

As used herein, the term "caliper" refers to the thickness of a substrate under a defined load, e.g. at 2.06 kPa.

As used herein, the term "machine direction" (or MD) is the direction parallel to the flow of a material through a manufacturing line.

As used herein, the term "cross-machine direction" (or CD) is the direction perpendicular to the machine direction.

As used herein, the term "intensive properties" are properties which do not have a value dependent upon an aggregation of values within the plane of the fibrous substrate. A common intensive property is an intensive property possessed by more than one region or zone. Such intensive properties of the fibrous substrate comprise, without limitation, average density, basis weight, elevation, caliper, and opacity. For example, if average density is a common intensive property of two differential regions, a value of the average density in one region or zone can differ from a value of the average density in the other region or zone. Regions or zones (such as, for example, a first region and a second region) are identifiable areas distinguishable from one another by distinct intensive properties.

As used herein, the term "substantially continuous" regions refers to an area within which one can connect any two points by an uninterrupted line running entirely within that area throughout the line's length. That is, the substantially continuous region has a substantial "continuity" in all directions parallel to the first plane and is terminated only at edges of that region. The term "substantially," in conjunction with continuous, is intended to indicate that while an absolute continuity is preferred, minor deviations from the absolute continuity may be tolerable as long as those deviations do not appreciably affect the performance of the fibrous substrates (or a papermaking belt) as designed and intended.

As used herein, the term "substantially semi-continuous" regions refer to an area which has "continuity" in all, but at least one, directions parallel to the first plane, and in which area one cannot connect any two points by an uninterrupted line running entirely within that area throughout the line's length. The semi-continuous framework may have continuity only in one direction parallel to the first plane. By analogy with the continuous region, described above, while an absolute continuity in all, but at least one, directions is preferred, minor deviations from such a continuity may be tolerable as long as those deviations do not appreciably affect the performance of the fibrous substrate.

As used herein, the term "discrete regions" refer to regions that are discontinuous and separated from other areas in all directions parallel to the first plane.

As used herein, the term "papermaking belt" refers to a structural element that is used as a support for the fiber or filaments that may be deposited thereon during a process of making a fibrous substrate, and as a forming unit to form a desired microscopical geometry of a fibrous substrate. The papermaking belt may comprise any element that has the ability to impart a three-dimensional pattern to the fibrous substrate being produced thereon, and includes, without limitation, a stationary plate, a belt, a cylinder/roll, a woven fabric, and a band.

As used herein, the term "basis weight" refers to the weight per unit area of a sample reported in gsm and is measured according to the Basis Weight Test Method described herein.

As used herein, the terms "substantially free of absorbent material" and "substantially absorbent material free" mean that the basis weight of the absorbent material in the substantially absorbent material free areas is at least less than 10%, in particular less than 5%, or less than 2%, of the basis weight of the absorbent material in the rest of the absorbent core.

As used herein, the terms "filament" or "fiber" refers to an elongate particulate having a length greatly exceeding its diameter, i.e. a length to diameter ratio of at least about 10.

General Description of an Absorbent Article

Figure 3:
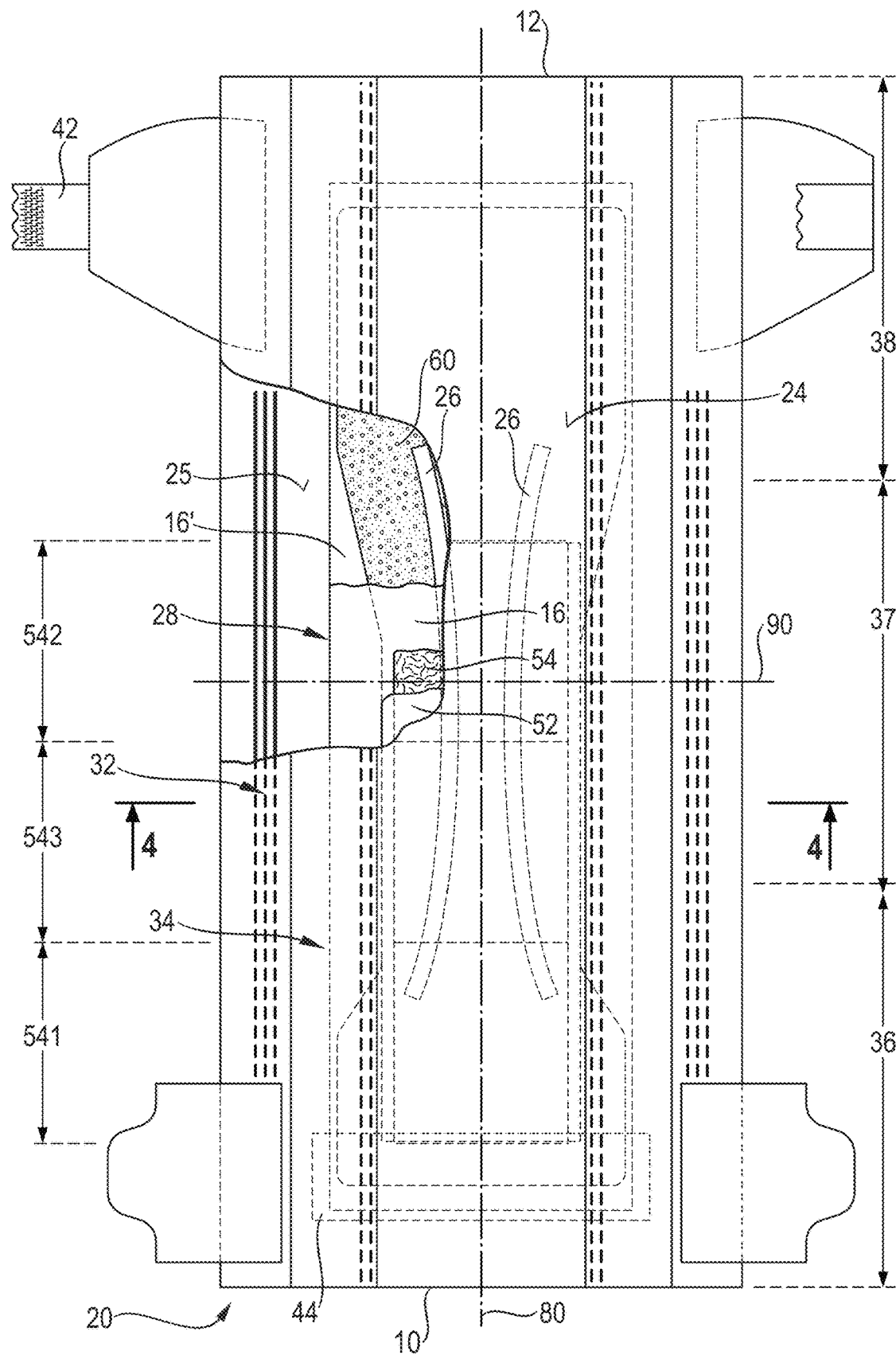
FIG. 3 is a top view of an absorbent article in the form of a diaper with some layers partially removed and comprising a distribution material in accordance with the present disclosure.

Referring to FIGS. 1 and 3, example absorbent articles 20 are disclosed. FIGS. 1 and 3 are top plan views of the absorbent articles 20, in a flat-out state, with portions of the structure being cut-away to more clearly show the construction of the absorbent articles 20. These absorbent articles 20 are shown for illustrative purposes only as the present disclosure may be used for making a wide variety of diapers or other absorbent articles. The absorbent article of FIG. 1 has a different core structure as the absorbent article of FIG. 3, as will be explained further below.

The absorbent article 20 may comprise a liquid permeable topsheet 24, a liquid impermeable backsheet 25, an absorbent core 28 positioned at least partially intermediate the topsheet 24 and the backsheet 25, and a distribution material comprising a three-dimensional, fibrous substrate comprising pulp fibers. The absorbent article 20 comprises a front edge or waist edge 10, a back edge or waist edge 12, and two longitudinal side edges 13. The front edge 10 is the edge of the absorbent article 20 which is intended to be placed towards the front of the user when worn, and the back edge 12 is the opposite edge. The absorbent article 20 may be divided by a longitudinal axis 80 extending from the front edge 10 to the back edge 12 of the absorbent article 20 and dividing the absorbent article 20 in two substantially symmetrical halves relative to the longitudinal axis, when viewing the absorbent article 20 from the wearer-facing side in a flat, laid out configuration, as illustrated in FIGS. 1 and 3.

Figure 2:
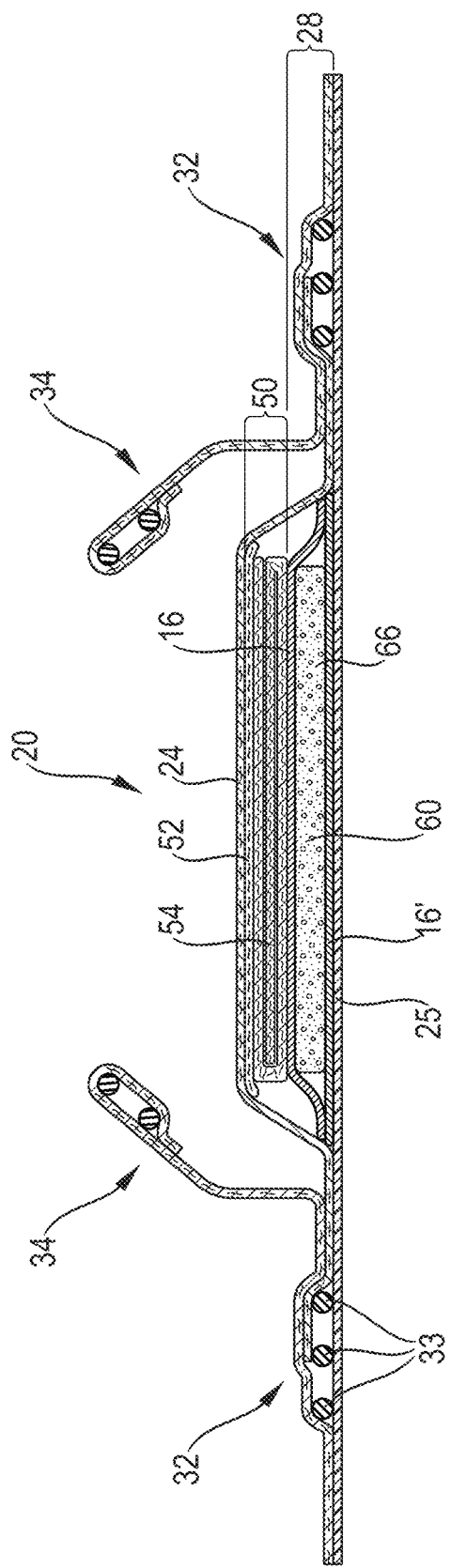
FIG. 2 is a cross-sectional view of the absorbent article, taken about line 2-2 of FIG. 1, in accordance with the present disclosure.

The absorbent article 20 may comprises a distribution material 54 comprising a three-dimensional fibrous substrate and may further comprise an acquisition layer or material 52 which may be placed on top of the distribution material 54 (the acquisition and distribution material are collectively referred to as acquisition-distribution system "ADS", designated as 50 in FIG. 2). In other forms, the absorbent articles may only comprise a distribution material and no acquisition layer. The absorbent article 20 may comprise elasticized gasketing cuffs 32 and upstanding barrier leg cuffs 34. FIGS. 1-4 also show other typical taped diaper components such as a fastening system comprising fastening tabs 42 positioned proximate to the back edge 12 of the absorbent article 20 and cooperating with a landing zone 44 positioned proximate to the front edge 10 of the absorbent article 20. The absorbent article 20 may also comprise other typical components, which are not represented in the Figures, such as a back elastic waist feature, a front elastic waist feature, transverse barrier cuff(s), and/or a lotion application, for example.

The absorbent article 20 may be divided by a lateral axis 90 into a front region and a back region of equal length measured along the longitudinal axis 80, when the absorbent article 20 is in a flat, laid-out state. The absorbent article's lateral axis 90 is perpendicular to the longitudinal axis 80 and is placed at half the longitudinal length of the absorbent article 20.

The absorbent article 20 may be divided into a front region 36, a back region 38 and a crotch region 37 located between the front region 36 and the back region 38 of the absorbent article 20. Each of the front, back and crotch regions are ⅓ of the longitudinal length of the absorbent article 20.

The topsheet 24, the backsheet 25, the absorbent core 28 and the other absorbent article components may be assembled in a variety of well known configurations, in particular by adhesive bonding and/or heat and/or pressure embossing. Example diaper assemblies are for example generally described in U.S. Pat. No. 3,860,003, U.S. Pat. No. 5,221,274, U.S. Pat. No. 5,554,145, U.S. Pat. No. 5,569,234, U.S. Pat. No. 5,580,411, and U.S. Pat. No. 6,004,306.

The absorbent core 28 may comprise an absorbent material 60 that is a blend of cellulosic fibers (so called "airfelt") and superabsorbent polymers in particulate form encapsulated in one or more substrates, see for example U.S. Pat. No. 5,151,092 to Buell. Alternatively, the absorbent core 28 may be free of airfelt, or substantially free of airfelt, as described in further detail herein.

Absorbent Core

The absorbent core 28 may comprise an absorbent material 60 with a high amount of superabsorbent polymers (SAP) enclosed within a core wrap. The absorbent material 60 may comprise from about 80% to about 100%, about 85% to about 100%, about 90% to about 100%, about 85%, about 90%, about 95%, or about 100%, specifically reciting all 1% increments within the above-specified ranges and all ranges formed therein or thereby, of SAP, such as SAP particles, by weight of the absorbent material 60. The core wrap is not considered as an absorbent material 60 for the purpose of assessing the percentage of SAP in the absorbent core 28.

The term "absorbent material" refers to a material which has at least some absorbency and/or liquid retaining properties, such as SAP, cellulosic fibers as well as some hydrophilically treated synthetic fibers. Typically, adhesives used in making absorbent cores have no absorbency properties and are not considered as absorbent material. The high SAP content of the absorbent material, as discussed above, may provide a relatively thin absorbent core 28 compared to conventional absorbent cores typically comprising between 40-60% SAP and 40-60% of cellulosic fibers. The absorbent material 60 may in particular comprise less than 15% weight percent, less than 10% weight percent, less than 5% weight percent, less than 3% weight percent, less than 1% weight percent, or may even be substantially free of natural and/or synthetic fibers. FIGS. 1 and 2 are illustrations of an absorbent article 20 comprising an "airfelt-free" absorbent core 28.

"Airfelt-free" absorbent cores 28 comprising relatively high amount of SAP with various absorbent core designs have been proposed in U.S. Pat. No. 5,599,335 (Goldman), EP1447066A1 (Busam), WO 95/11652 (Tanzer), U.S. Pat. No. 5,650,214 (Handoff), and WO 2012/052172 (Van Moldered).

The absorbent core 28 may comprise one or more adhesives to help immobilize the SAP within the core wrap and/or to ensure integrity of the core wrap, in particular when the core wrap is made of one or more substrates. In one form, the core wrap may extend over a larger area than strictly needed for containing the absorbent material 60 within.

Core Wrap

Again referring to FIGS. 1-4, the absorbent material 60 may be at least partially encapsulated in one or more substrates.

Figure 4:
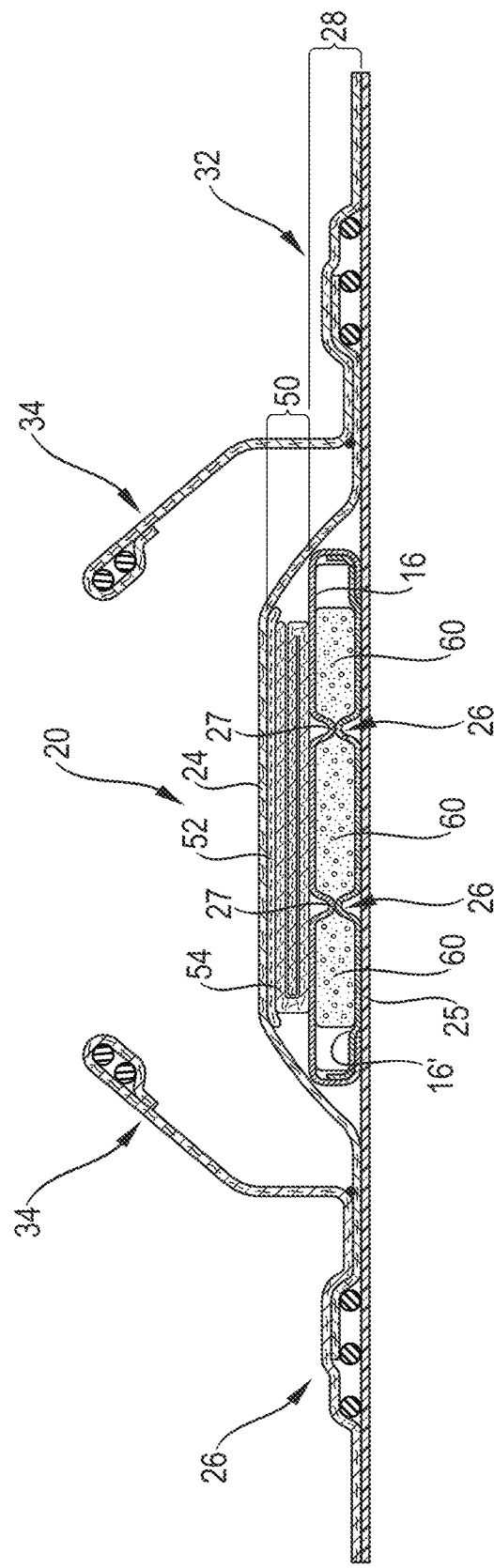
FIG. 4 is a cross-sectional view of the absorbent article, taken about line 4-4 of FIG. 3, in accordance with the present disclosure.

The core wrap may comprise a top side 16 facing the topsheet 24 and a bottom side 16' facing the backsheet 25. The core wrap may be made of a single substrate folded around the absorbent material 60. Alternatively, the core wrap may be made of two substrates (one mainly providing the top side 16 and the other mainly providing the bottom side 16') which are attached to another, as shown in the example of FIG. 2. Typical configurations of the core wrap are the so-called C-wrap and/or sandwich wrap. Referring to FIG. 4, in a C-wrap, the longitudinal and/or lateral edges of one of the substrates may be folded over another substrate to form flaps. These flaps may then be bonded to the external surface of the other substrate, typically by bonding with one or more adhesives.

The core wrap may be formed by any materials suitable for receiving and containing the absorbent material 60. Typical substrate materials used in the production of conventional absorbent cores may be used, in particular fibrous substrates made of wet-laid fibers, films, wovens or nonwovens, or laminate of any of these. The core wrap may in particular be formed by a nonwoven web, such as a carded nonwoven, spunbond nonwoven ("S") or meltblown nonwoven ("M"), and laminates of any of these. For example, spunmelt polypropylene nonwovens are suitable, in particular those having a laminate web SMS, or SMMS, or SSMMS, structure, and having a basis weight range of about 5 gsm to 20 gsm. Suitable materials are, for example, disclosed in U.S. Pat. No. 7,744,576, U.S. Pat. Publ. No. 2011/0268932A1, U.S. Pat. Publ. No. 2011/0319848A1, or U.S. Pat. Publ. No. 2011/0250413A1. Nonwoven materials provided from synthetic fibers may also be used, such as PE, PET and in particular PP.

When the core wrap is made of two (or more) substrates, the two (or more) substrates of the core wrap may be made of the same type of material, or may be made of different materials or one of the substrates may be treated differently than the other to provide it with different properties. At least the substrate facing the topsheet 24 may be made of a nonwoven web.

The top side 16 of the core wrap may be sealed to the bottom side 16' of the core wrap at least partially along all the edges of the absorbent core 28. The term "seal" is to be understood in a broad sense. The seal does not need to be continuous along the whole periphery of the core wrap, but may be discontinuous along part or the whole of it, such as formed by a series of closely spaced apart seal points on a line. Typically, a seal may be formed by adhesive bonding and/or thermal bonding.

When the core wrap is formed by two substrates, one seal per edge of the absorbent core 28 may typically be used to enclose the absorbent material 60 within the core wrap. As illustrated in FIG. 4, for example, a first substrate including the top side 16 of the core wrap may be placed on one side of the absorbent core 28 and extends around the absorbent core's longitudinal edges to at least partially wrap an opposed bottom side of the absorbent core 28. A second substrate comprising the bottom side 16' of the core wrap may be present between the wrapped flaps of the first substrate of the core wrap and the absorbent material 60 of the absorbent core 28. The flaps of the first substrate of the core wrap may be adhesively bonded to the second substrate of the core wrap to provide a seal. This so called C-wrap construction may provide benefits such as improved resistance to bursting in a wet loaded state compared to a sandwich seal. A front edge and back edge of the core wrap may then also be sealed, for example, by bonding the first substrate and second substrate of the core wrap, flat to another to provide more complete enclosure of the absorbent material 60 across the whole of the periphery of the absorbent core 28. In the so-called sandwich construction, the first and second substrates of the core wrap may also extend outwardly on all edges of the absorbent core 28 and be sealed flat along the whole or parts of the periphery of the absorbent core 28, typically by adhesive bonding and/or heat/pressure bonding. In other forms, the core wrap may also be formed by a single substrate which may enclose, as in a parcel wrap, the absorbent material 60.

"Airfelt-Free" Absorbent Core Having One or More Substantially Material Free Areas Referring generally to FIGS. 3 and 4, the absorbent core 28 may comprise an absorbent material deposition area defined by the periphery of the layer formed by the absorbent material 60 within the core wrap.

The absorbent core 28 may comprise one or more substantially absorbent material free area(s) 26 or absorbent material free areas 26 (hereinafter together referred to as "substantially absorbent material free area(s)") which is/are substantially free of, or free of, absorbent material 60 and through which a portion of the top side 16 of the core wrap is attached by one or more core wrap bond(s) 27 to a portion of the bottom side 16' of the core wrap. In particular, there may be no absorbent material 60 in these areas. Minimal amounts such as contaminations with absorbent material 60 that may occur during the making process are not considered as absorbent material 60. The one or more substantially absorbent material free area(s) 26 is/are advantageously confined by the absorbent material 60, which means that the substantially absorbent material free area(s) 26 do(es) not extend to any of the edge of the absorbent material deposition area.

The portions of the top side 16 and the bottom side 16' of the core wrap may be attached together continuously along the substantially absorbent material free area(s) 26. However, one or more core wrap bonds 27 along the substantially absorbent material free area(s) 26 may also be discontinuous (intermittent) such as series of point bonds. The core wrap bond(s) (27) may be provided by known attachment methods, such as adhesive bonding, pressure bonding, ultrasonic bonding, heat bonding, dynamic mechanical bonding, or combinations thereof.

The attachment of the portions of the top side 16 and the bottom side 16' of the core wrap may be provided by one or more adhesives, in particular one or more layers of adhesive and/or one or more layers of fibrous adhesive material, if present in the absorbent core 28. These adhesives may therefore serve the dual function of immobilizing the absorbent material 60 and attaching the top side 16 of the core wrap to the bottom side 16' of the core wrap within one or more substantially absorbent material free area(s) 26.

In one form, the absorbent core 28 may comprise at least two substantially absorbent material free areas 26 symmetrically disposed on both sides of the longitudinal axis 80 or the lateral axis 90.

The substantially absorbent material free area(s) 26 may be straight and completely oriented longitudinally and parallel to the longitudinal axis 80, but also may be curved or have one or more curved portions. The substantially absorbent free area(s) 26 may also be oriented parallel to the lateral axis 90 or may be oriented in any other suitable direction.

Furthermore, in order to reduce the risk of liquid bodily exudate leakages, the substantially absorbent material free area(s) 26 advantageously do not extend to any of the edges of the absorbent material deposition area, and, therefore, may be surrounded by and fully encompassed within the absorbent material deposition area of the absorbent core 28. As an example, the smallest distance between a substantially absorbent material free area 26 and the closest edge of the absorbent material deposition area may be at least about 2 mm or at least about 5 mm, although other distances may also be suitable.

"Airfelt-free" absorbent cores 28 comprising substantially absorbent material free areas 26 have been proposed, see for example EP Patent Application No. 12196341.7.

Figure 5:
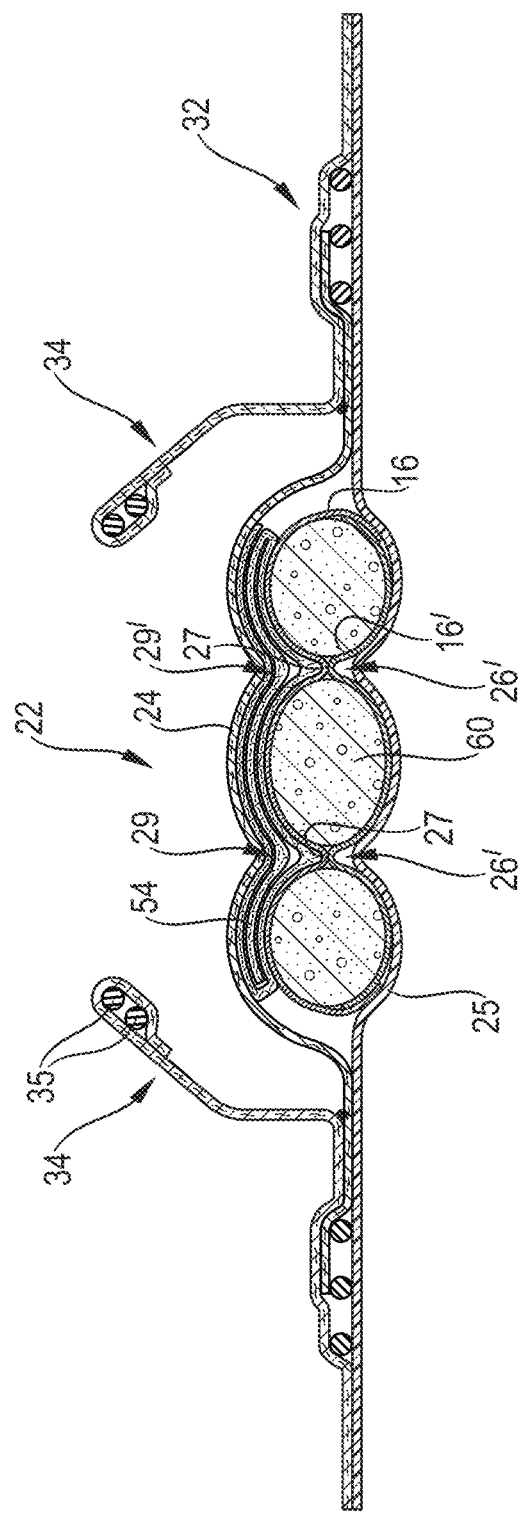
FIG. 5 is a cross-sectional view of the absorbent article, taken about line 4-4 of FIG. 3, where channels have formed as a result the absorbent article being loaded with liquid bodily exudates in accordance with the present disclosure.

Referring to FIG. 5, one or more channel(s) 26' along the substantially absorbent material free area(s) 26 in the absorbent core 28 may start forming when the absorbent material 60 absorbs one or more liquid bodily exudates and begins to swell. As the absorbent core 28 absorbs more liquid, the depressions within the absorbent core 28 formed by the channel(s) 26' may become deeper and more apparent to the eye and the touch. The formation of the channel(s) 26' may also serve to indicate that the absorbent article 20 has been loaded with liquid bodily exudates. The core wrap bond(s) 27 should remain substantially intact at least during a first phase as the absorbent material 60 absorbs a moderate quantity of liquid bodily exudates (e.g., urine, menses, runny BM).

As shown in FIG. 5, when the absorbent material 60 swells, the core wrap bonds 27 remain at least initially attached in the substantially absorbent material free areas 26. The absorbent material 60 swells in the rest of the absorbent core 28 when it absorbs liquid bodily exudates, so that the core wrap thus forms channels 26' along the substantially absorbent material free areas 26 comprising the core wrap bonds 27.

When the absorbent material 60 in the absorbent core 28 swells, so that the channels 26' form, the surface of the top side 16 of the core wrap may become uneven, see FIG. 5. As the distribution material 54 is placed on top of the top side 16 of the core wrap, the distribution material 54 may follow the uneven surface of the top side 16. The formation of the channels 26' may create indentations where portions of the distribution material 54 may sink into these indentations. This may promote the formation of disruptions of the distribution material 54, when the distribution material 54 is an air-laid material and in a wet state during use. Hence, "airfelt-free" absorbent cores 28 comprising substantially absorbent material free areas 26 may promote more disruptions in the distribution material 54 when the absorbent material 60 swells.

To solve such a problem, a distribution material 54 comprising a fibrous substrate comprising wet-laid or wet-formed fibers having sufficient wet burst strength, especially a fibrous substrate having a wet burst strength from about 50 g to about 500 g or from about 250 g to about 350 g or from about 300 g to about 350 g according to the Wet Burst Test Method as disclosed herein, may be provided to achieve a more wet integrate distribution material. The distribution material 54 may comprise pulp fibers.

Distribution Material

The absorbent article 20 may comprise a distribution material 54 positioned at least partially between the topsheet 24 and a wearer-facing side the absorbent core 28. In another form, the distribution material 54 may instead be provided between an acquisition material and the wearer-facing side of the absorbent core 28. In another form, the distribution material 54 may be provided between the topsheet 24 and an acquisition material. In yet another form, the distribution material may be provided between the backsheet 25 and a garment-facing side of the absorbent core 28.

Referring to FIGS. 1 and 3, the distribution material 54 may comprise a front region 541, a back region 542, and a middle region 543 located between the front region 541 and the back region 542. Each of the front, back and middle regions 541, 542, and 543 may be ⅓ of the longitudinal length of the distribution material 54. The distribution material may have a first profile in the front region 541, the crotch region 543, and/or the back region 542 and may have a second, different profile in one or more of the other regions 541, 542, 543. In other instances, all regions may have a different profile or the same profile. In still other instances, at least one region may have a different profile as the remaining two regions.

The distribution material 54 has a longitudinal axis which may coincide with the longitudinal axis 80 of the absorbent article 20 and a lateral axis (both not shown) intersecting a midpoint of the longitudinal axis of the distribution material 54. The intersection of the longitudinal and lateral axes of the distribution material 54 defines the center of the distribution material 54. The distribution material 54 may comprise a front edge, a back edge, and two longitudinal side edges. The distribution material 54 may comprise a three-dimensional fibrous substrate comprising about 70% to about 100% (specifically reciting all 1% increments within the specified range and all ranges formed therein), at least 80%, at least 85%, at least 90%, at least 95%, or at least 99% pulp fibers by weight of the three-dimensional fibrous substrate Wet-Laid Fibers At least a portion of, or all of the distribution material 54 may comprise one or more substrates or more than one layer of a fibrous substrate. At least one of the substrates may comprise a wet-laid, three-dimensional fibrous substrate 55 (see FIG. 10) comprising at least 80% pulp fibers by weight of the fibrous substrate. In some forms, some of, or all of, the front, middle, and/or back regions 541, 542, and 543 may comprise one or more layers of fibrous substrates.

The wet-laid fibers may comprise cellulosic fibers, such as pulp fibers. The wet-laid fibers may be produced by forming a predominantly aqueous slurry comprising about 90% to about 99.9% water or other suitable fluid or liquid. In one form, the non-aqueous component of the slurry used to make the wet-laid and/or wet-formed fibers may comprise from about 1% to about 95% or about 5% to about 80% of cellulosic fibers, such as eucalyptus fibers, by weight of the non-aqueous components of the slurry. In another form, the non-aqueous components may comprise from about 8% to about 60% of cellulosic fibers, such as eucalyptus fibers, by weight of the non-aqueous components of the slurry, or from about 15% to about 30% of cellulosic fibers, such as eucalyptus fibers, by weight of the non-aqueous component of the slurry. In some instances, the slurry may comprise about 45% to about 60% of Northern Softwood Kraft fibers with up to 20% Southern Softwood Kraft co-refined together, about 25% to about 35% unrefined Eucalyptus fibers and from about 5% to about 30% of either repulped product broke or thermomechanical pulp. Any other suitable cellulosic fibers and/or combinations thereof within the knowledge of those of skill in the art may also be used.

The wet-laid fibers may comprise a mixture of at least two different materials. At least one of the materials may comprise a non-naturally occurring fiber, such as a polypropylene fiber or a polyolefin fiber, for example, and at least one other material, different from the first material, comprising a solid additive, such as another fiber and/or a particulate, for example.

Synthetic fibers useful herein may comprise any suitable material, such as, but not limited to polymers, those selected from the group consisting of polyesters, polypropylenes, polyethylenes, polyethers, polyamides, polyhydroxyalkanoates, polysaccharides, and combinations thereof. More specifically, the material of the polymer segment may be selected from the group consisting of poly(ethylene terephthalate), poly(butylene terephthalate), poly(1,4-cyclohexylenedimethylene terephthalate), isophthalic acid copolymers (e.g., terephthalate cyclohexylene-dimethylene isophthalate copolymer), ethylene glycol copolymers (e.g., ethylene terephthalate cyclohexylene-dimethylene copolymer), polycaprolactone, poly(hydroxyl ether ester), poly (hydroxyl ether amide), polyesteramide, poly(lactic acid), polyhydroxybutyrate, and combinations thereof.

Further, the synthetic fibers may be a single component fibers (i.e., single synthetic material or a mixture to make up the entire fiber), multi-component fibers, such as bi-component fibers (i.e., the fiber is divided into regions, the regions including two or more different synthetic materials or mixtures thereof), and combinations thereof. Nonlimiting examples of suitable bicomponent fibers are fibers made of copolymers of polyester (polyethylene terephthalate/ isophtalate/polyester (polyethylene terephthalate) otherwise known as "CoPET/PET" fibers, which are commercially available from Fiber Innovation Technology, Inc., Johnson City, Tenn.

Non-Wood Pulp Fibers

The pulp fibers may also comprise non-wood fibers.

Non-wood fibers may comprise fibers made from polymers, specifically hydroxyl polymers. Non-limiting examples of suitable hydroxyl polymers include polyvinyl alcohol, starch, starch derivatives, chitosan, chitosan derivatives, cellulose derivatives, gums, arabinans, galactans, and combinations thereof. Additionally, other synthetic fibers such as rayon, polyethylene, and polypropylene fibers can be used within the scope of the present disclosure. Other suitable materials are also intended to be within the scope of the present disclosure.

Non-wood pulp fibers may also comprise fibers that comprise processed residuals from agricultural crops such as wheat straw, wetland non-tree plants such as bulrush, aquatic plants such as water hyacinth, microalgae such as *Spirulina* and macroalgae seaweeds such as red or brown algae. Examples of non-wood natural materials include, but are not limited to, wheat straw, rice straw, flax, bamboo, cotton, jute, hemp, sisal, bagasse, hesperaloe, switchgrass, miscanthus, marine or fresh water algae/seaweeds, and combinations thereof.

Optional Ingredients

To enhance permanent wet strength of one or more fibrous substrates of the distribution material 54, cationic wet strength resins may be added to the papermaking furnish or to the embryonic web. The fibrous substrate made of wet-laid fibers may comprise one or more cationic wet strength resins selected from the group consisting of a base activated epoxide polyamide epichlorohydrin resin, an urea-formaldehyde resin, a melamine formaldehyde resin, a polyamide-epichlorohydrin resin, a polyethyleneimine resin, a polyacrylamide resin, a dialdehyde starch and mixtures thereof.

From about 0.90 kg/ton to about 2.27 kg/ton, from about 0.22 kg/ton to about 13.6 kg/ton, or from about 4.53 kg/ton to about 11.34 kg/ton of dry paper fibers of the cationic wet strength resin may be used.

The cationic wet strength resins may comprise cationic water soluble resins. These resins may improve wet strength in a fibrous substrate. This resin may improve either temporary or permanent wet strength to the fibrous substrate. KYMENE® resins obtainable from Hercules Inc., Wilmington, Del. may be used, including KYMENE® 736 which is a polyethyleneimine (PEI) wet strength polymer. It is believed that the PEI may improve wet strength by ionic bonding with the pulps carboxyl sites. KYMENE® 557LX is polyamide epichlorohydrin (PAE) wet strength polymer. It is believed that the PAE contains cationic sites that may lead to resin retention by forming an ionic bond with the carboxyl sites on the pulp. The polymer contains 3-azetidinium groups which react to form covalent bonds with the pulps' carboxyl sites as well as with the polymer backbone. The product may undergo curing in the form of heat or undergo natural aging for the reaction of the azentidinium group. KYMENE® 450 is a base activated epoxide polyamide epichlorohydrin polymer. It is theorized that like 557LX the resin attaches itself ionically to the pulps' carboxyl sites. The epoxide group is much more reactive than the azentidinium group. The epoxide group reacts with both the hydroxyl and carboxyl sites on the pulp, thereby giving higher wet strengths. The epoxide group may also crosslink to the polymer backbone. KYMENE® 2064 is also a base activated epoxide polyamide epichlorohydrin polymer. It is theorized that KYMENE® 2064 may improve its wet strength by the same mechanism as KYMENE® 450. KYMENE® 2064 differs in that the polymer backbond contains more epoxide functional groups than does KYMENE® 450. Both KYMENE® 450 and KYMENE® 2064 may require curing in the form of heat or natural aging to fully react all the epoxide groups, however, due to the reactiveness of the epoxide group, the majority of the groups (80-90%) react and improve wet strength off the paper machine. Mixtures of the foregoing may be used. Other suitable types of such resins include urea-formaldehyde resins, melamine formaldehyde resins, polyamide-epichlorohydrin resins, polyethyleneimine resins, polyacrylamide resins, dialdehyde starches, and mixtures thereof. Other suitable types of such resins are described in U.S. Pat. No. 3,700,623, issued Oct. 24, 1972; U.S. Pat. No. 3,772,076, issued Nov. 13, 1973; U.S. Pat. No. 4,557,801, issued Dec. 10, 1985 and U.S. Pat. No. 4,391,878, issued Jul. 5, 1983.

The cationic wet strength resin may be added at any point in the process, where the resin will come in contact with the fibers prior to forming the wet web.

Structure of a Three-Dimensional Fibrous Substrate

Figure 6:
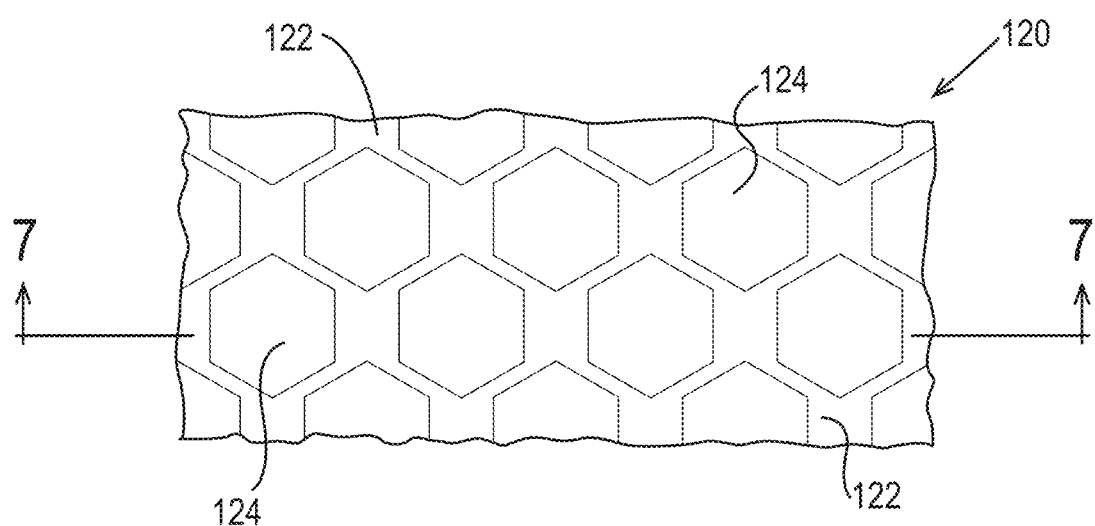
FIG. 6 is an example plan view of a wet-laid and wet-formed, three-dimensional fibrous substrate of a distribution material in accordance with the present disclosure.
Figure 7:
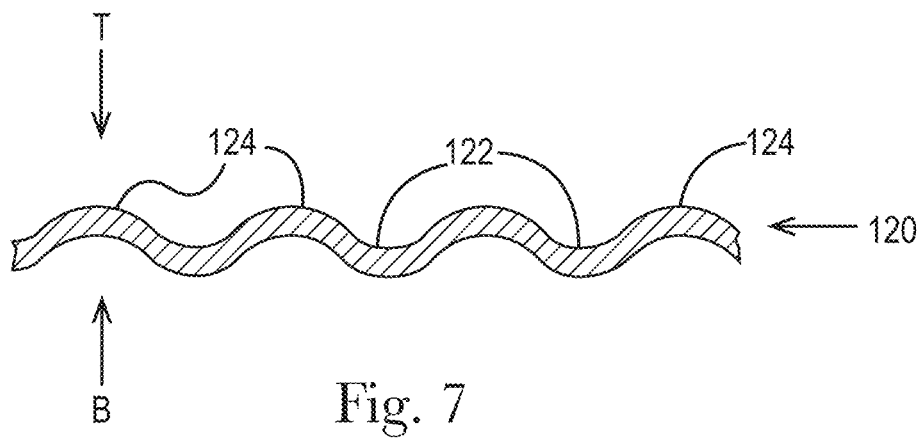
FIG. 7 is a cross-sectional view of the three-dimensional fibrous substrate taken about line 7-7 of FIG. 6, in accordance with the present disclosure.

Referring to FIGS. 6 and 7, a three-dimensional fibrous substrate 120 may be formed that has at least a first region (e.g., a continuous network region 122) and a second region (e.g., a plurality of discrete zones 124). The continuous network region 122 may be raised or indented (out of or into the page) relative to the plurality of discrete zones 124. Stated another way, the continuous network region 122 may form a high density zone and the plurality of discrete zones 124 may form a low density zone or the continuous network region 122 may form a low density zone and the plurality of discrete zones 124 may form a high density zone. Regardless of whether each of the regions or discrete zones is high or low density, the plurality of discrete zones 124 may be dispersed throughout and/or formed within the continuous network region 122. In one form, the continuous network region 122 may have a first average density and the plurality of discrete zones may have a second, different average density, according to the Average Density Test Method herein. Although referred to herein as a "continuous network region", as an example, it will be understood that the "network region" may be substantially continuous or substantially semi-continuous. Herein the network region will be referred to as "continuous" as an example and not to limit the present disclosure. The network region may also be discontinuous in some forms.

Each of the continuous network region 122 and the plurality of discrete zones 124 may have at least one common intensive property, such as, for example, basis weight, caliper, elevation, opacity, and/or average density. The common intensive property of the continuous network region 122 may have a first value and the plurality of discrete regions may have a second value. The first value may be different than the second value. For example, the average density of the continuous network region 122 may be higher than the average density of the plurality of discrete zones 124. FIG. 6 illustrates a plan view a portion of the fibrous substrate 120 where the continuous network region 122 is illustrated as defining hexagons, although it is to be understood that other preselected patterns may also be used.

Each of the continuous network region 122 and the plurality of discrete zones 124 may have a second common intensive property, such as, for example, basis weight, caliper, elevation, opacity, and/or average density. The second common intensive property of the continuous network region 122 may have a first value and the plurality of discrete regions may have a second value. The first value may be different than the second value.

In one instance, the continuous network region may have first and second common intensive properties with the plurality of discrete zones. The first common intensive property may be average density or basis weight and the second common intensive property may be caliper, elevation or opacity, for example.

FIG. 7 is a cross-sectional view of the fibrous substrate 120 taken along line 7-7 of FIG. 6. As can be seen from the example of FIG. 7, the continuous network region 122 is essentially monoplanar. The plurality of discrete zones 124 are dispersed throughout the entire continuous network region 122 and essentially each discrete zone 124 is encircled by the continuous network region 122. The shape of the discrete zones 124 may be defined by the continuous network region 122. As shown in FIG. 7, the discrete zones 124, appear to extend from (protrude from) the plane formed by continuous network region 122 toward an imaginary observer looking in the direction of arrow T of FIG. 7. When viewed by an imaginary observer looking in the direction indicated by arrow B of FIG. 7, the plurality of discrete zones 124 may comprise arcuately shaped voids which appear to be cavities or dimples.

Figure 8:
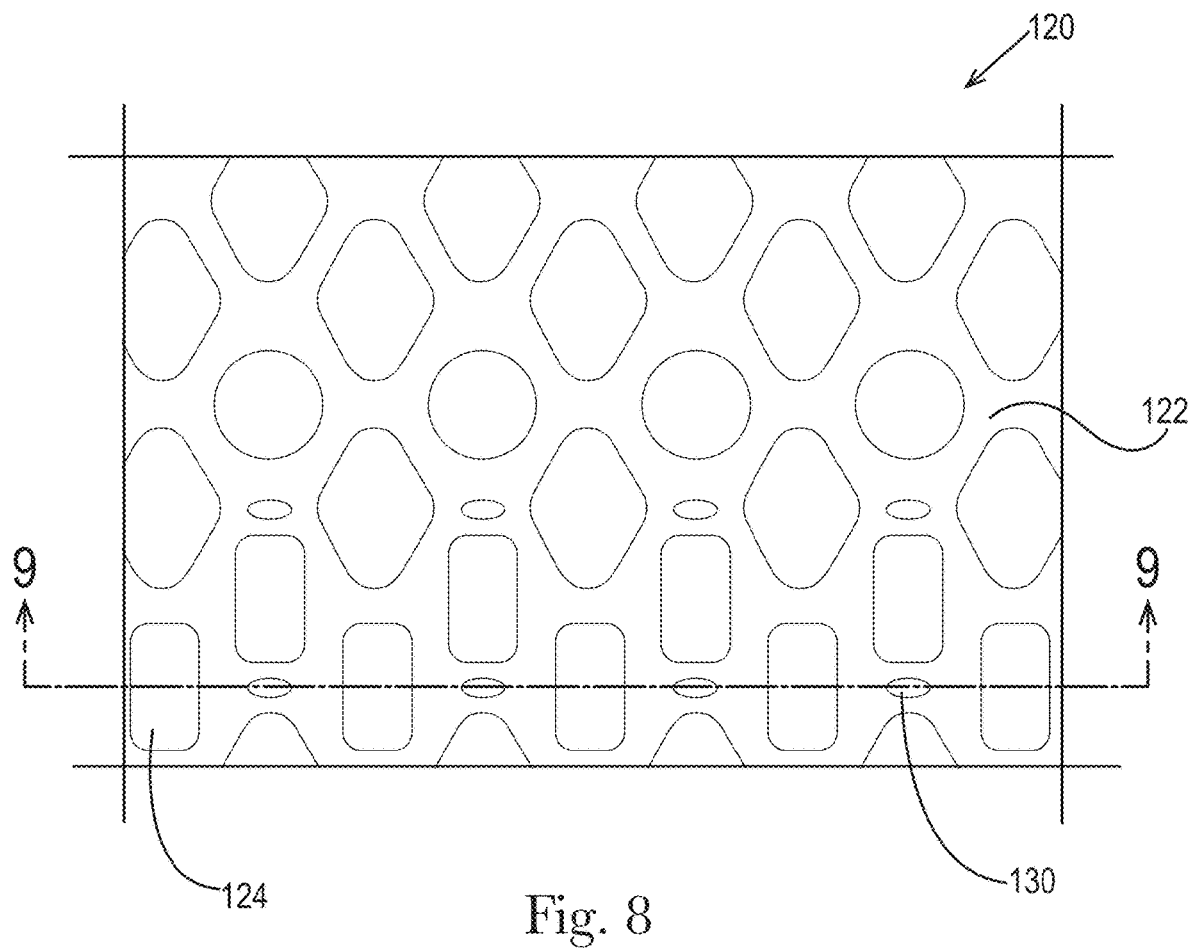
FIG. 8 is another example plan view of a wet-laid and wet-formed, three-dimensional fibrous substrate of the distribution material in accordance with the present disclosure.
Figure 9:
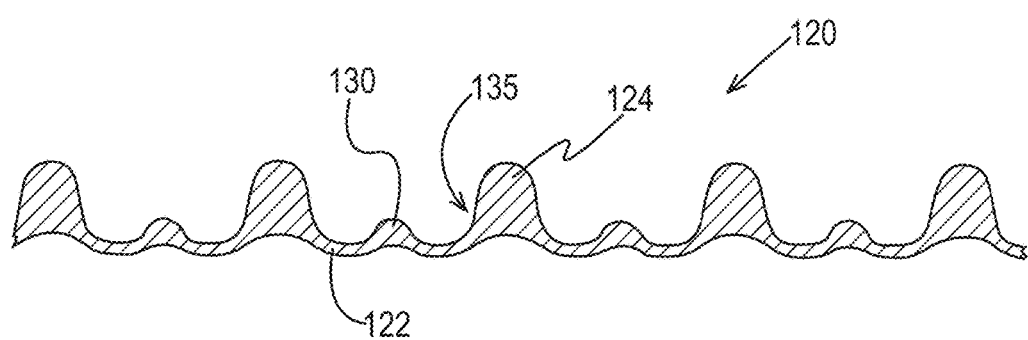
FIG. 9 is an cross-sectional view of the three-dimensional fibrous substrate taken about line 9-9 of FIG. 8, in accordance with the present disclosure.

Referring to FIGS. 8 and 9, the continuous network region 122 and the plurality of discrete zones 124 of the fibrous substrate 120 may also differentiate in their respective micro-geometry. In the example of FIGS. 8 and 9, the continuous network region 122 forms a first plane (knuckles or high density regions) at a first elevation when the fibrous substrate 120 is disposed on a flat surface and the plurality of discrete zones 124 are dispersed throughout the continuous network region 122. These discrete zones 124 may comprise discrete protuberances, or "pillows," (or low density regions) outwardly extending from the continuous network region 122 to form a second elevation greater than the first elevation, relative to the first plane. Alternatively, the continuous network region 122 may comprise the pillows or low density regions (higher elevation) and the plurality of discrete zones 124 may comprise the knuckles or high density regions (lower elevation) depending on how the papermaking belt is formed. It is to be understood that pillows and/or knuckles may also comprise a continuous pattern, a substantially continuous pattern, or a substantially semi-continuous pattern.

Referring again to FIGS. 8 and 9, the fibrous substrate 120 may comprise a third region 130 having at least one intensive property that is common with and differs in value from the intensive property of the continuous network region 122 and the intensive property of the plurality of discrete zones 124. For example, the continuous network region 122 may have a common intensive property having a first value, the plurality of discrete zones 124 may have the common intensive property having a second value, and the third region 130 may have the common intensive property having a third value, wherein the first value may be different from the second value, and the third value may be different from the second value and the first value. The common intensive property may be any of those specified herein. In one form, such a third region 130 may comprise one or more transition regions 135 (see FIG. 9) located between the continuous network region 122 and the plurality of discrete zones 124. The transition region 135 is the area or region between which the continuous network region 122 and the plurality of discrete zones 124 transition. Stated another way, the transition regions 135 are positioned intermediate the continuous network region 122 and the plurality of discrete zones 124. The continuous network region 122, the plurality of discrete zones 124, and the plurality of transition regions 135 may each have a first and/or second common intensive property. The first and/or second common intensive property of the continuous network region 122 may have a first value, the first and/or second common intensive property of the plurality of discrete zones 124 may have a second value, and the first and/or second common intensive property of the plurality of transition regions 135 may have a third value. The first and/or second common intensive property may be any of those specified herein, such as average density and basis weight, for example.

When the fibrous substrate 120 comprising at least three differential regions 122, 124, 130, as described herein, is disposed on a horizontal reference plane (e.g., the X-Y plane), the first region 122 may define a plane having a first elevation, and the second region 124 may extend therefrom to define a second elevation. One form is contemplated, in which the third region 130 defines a third elevation, wherein at least one of the first, second, and third elevations is different from at least one of the other elevations. For example, the third elevation can be intermediate the first and second elevations. It is to be noted that, in the alternative, the first region 122 may have the second elevation (highest) and the second region 124 may have the first elevation (lowest). The third region 130 may exist at an elevation intermediate the second and first elevations. The transitions regions may also exist in elevation intermediate any of the first, second and third regions.

Suitable fibrous substrates having a continuous network region and a plurality of discrete zones may have predetermined elevations. For example, in certain instances, one of the continuous network region or the plurality of discrete zones may have an elevation from about 50 microns to about 5000 microns; one of the continuous network region or the plurality of discrete zones may have an elevation from about 100 microns to about 2000 microns; or one of the continuous network region or the plurality of discrete zones may have an elevation from about 150 microns to about 1500 microns, according to the Topographic Measurements of Differential Density Fibrous Substrates Test herein.

The following table shows, without limitation, some possible combinations of forms of the fibrous substrate 120 comprising at least three regions having differential (i.e., high, medium, or low) intensive properties. All of these forms are included in the scope of the present disclosure.

| INTENSIVE PROPERITES | | |
|---|---|---|
| HIGH | MEDIUM | LOW |
| Continuous | Discontinuous | Discontinuous |
| Continuous | Discontinuous | — |
| Continuous | — | Discontinuous |
| Semi-continuous | Semi-continuous | Semi-continuous |
| Semi-continuous | Semi-continuous | Discontinuous |
| Semi-continuous | Semi-continuous | — |
| Semi-continuous | Discontinuous | Semi-continuous |
| Semi-continuous | Discontinuous | Discontinuous |
| Semi-continuous | — | Semi-continuous |
| Discontinuous | Continuous | Discontinuous |
| Discontinuous | Continuous | — |
| Discontinuous | Semi-continuous | Semi-continuous |
| Discontinuous | Semi-continuous | Discontinuous |
| Discontinuous | Discontinuous | Continuous |
| Discontinuous | Discontinuous | Semi-continuous |
| Discontinuous | Discontinuous | Discontinuous |
| Discontinuous | — | Continuous |
| — | Continuous | Discontinuous |
| — | Semi-continuous | Semi-continuous |
| — | Discontinuous | Continuous |

Suitable fibrous substrates as described herein may have continuous network regions and a plurality of discrete zones having different (e.g., not the same) average densities. The average density for either the continuous network region or the plurality of discrete zones may be from about 0.05 g/cc to about 0.80 g/cc, from about 0.10 g/cc to about 0.50 g/cc, or from about 0.15 g/cc to about 0.40 g/cc, according to the Average Density Test herein. In other forms, the average density of the continuous network region may be from about 0.05 g/cc to about 0.15 g/cc and the average density of the plurality of discrete zones may be from about 0.15 g/cc to about 0.80 g/cc; the average density of the continuous network region may be from about 0.07 g/cc to about 0.13 g/cc and the average density of the plurality of discrete zones may be from about 0.25 g/cc to about 0.70 g/cc; or the average density of the continuous network region may be from about 0.08 g/cc to about 0.12 g/cc and the average density of the plurality of discrete zones may be from about 0.40 g/cc to about 0.60 g/cc, according to the Average Density Test herein. All 0.01 g/cc increments within the above-cited ranges and any ranges formed there are expressly recited herein. In other instances, the average density values may be vice-versa for each of the continuous network region and the plurality of discrete zones. Considering the number of fibers underlying a unit area projected onto the portion of the fibrous substrate under consideration, the ratio of the average density of the continuous network region to the average density of the plurality of discrete zones can be greater than 1. In other forms, the ratio of the average density of the continuous network region to the average density of the plurality of discrete zones may be less than 1.

In an instance, the continuous network region and the plurality of discrete zones may each have a common intensive property. The common intensive property of the continuous network region may have a first value, while the common intensive property of the plurality of discrete zones may have a second value. The first value and the second value may be different. The common intensive property may be any of those specified herein or other common intensive properties.

In one instance, three-dimensional fibrous substrate may be creped or uncreped. The continuous network region may have a first basis weight and the plurality of discrete zones may have a second, different basis weight. The continuous network region may have a first caliper or elevation and the plurality of discrete zones may have a second caliper or elevation. The first and second calipers or elevations may be different. In other instances, the continuous network region may have a first average density and a first basis weight, while the plurality of discrete zones may have a second average density and a second basis weight. The first and second average densities and the first and second basis weights may be different. The same may apply to the third regions 130 and the transition regions 135, either relative to each other or relative to the continuous network region or the plurality of discrete zones.

Figure 10:
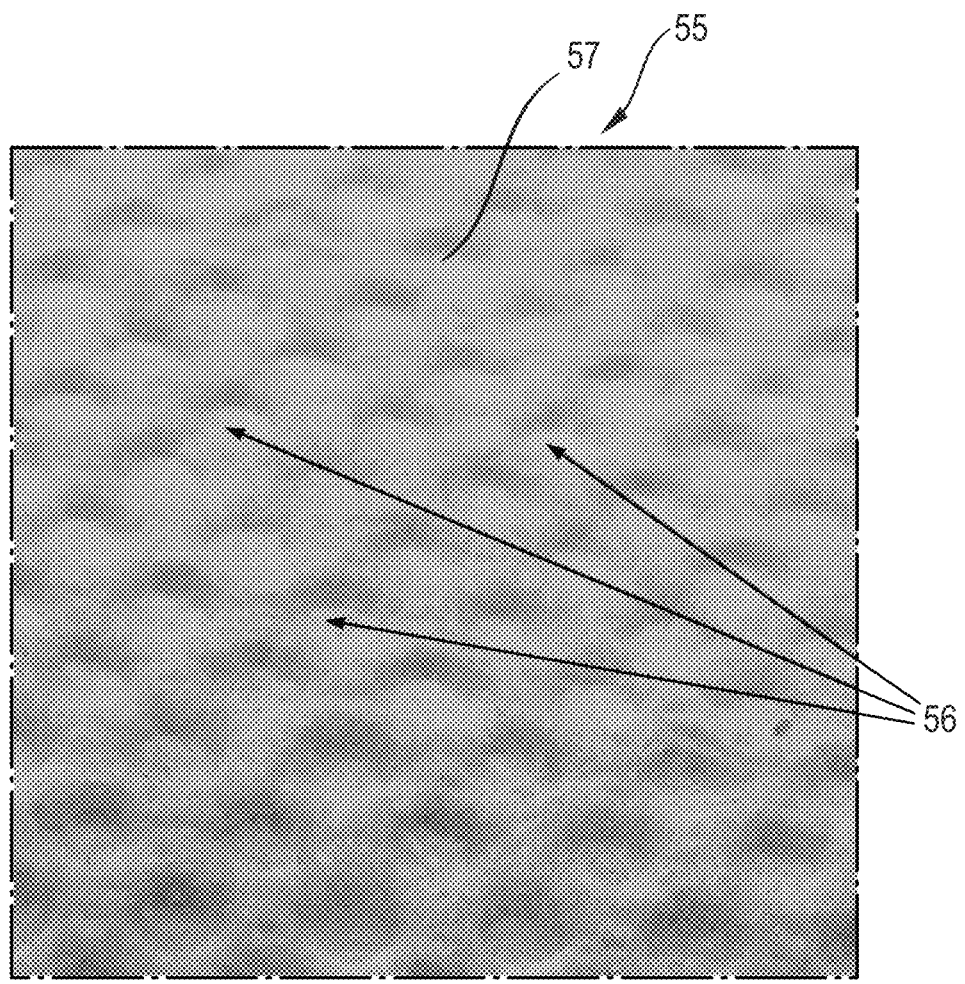
FIG. 10 is an example plan view of a portion of a wet-laid and wet-formed, three-dimensional fibrous substrate of a distribution material in accordance with the present disclosure.

Referring to FIG. 10, the distribution material 54 may comprise a fibrous substrate 55 formed from wet-laid and wet-formed fibers or filaments. A continuous network region 56 is illustrated as raised elements or pillow regions (low density regions) in FIG. 10, while a plurality of discrete zones 57 are illustrated as knuckle regions (high density regions). It will be recognized that any suitable number of layers of fibrous substrates 55 may be combined to form a distribution material or a portion thereof, as is described in further detail herein.

Figure 11:
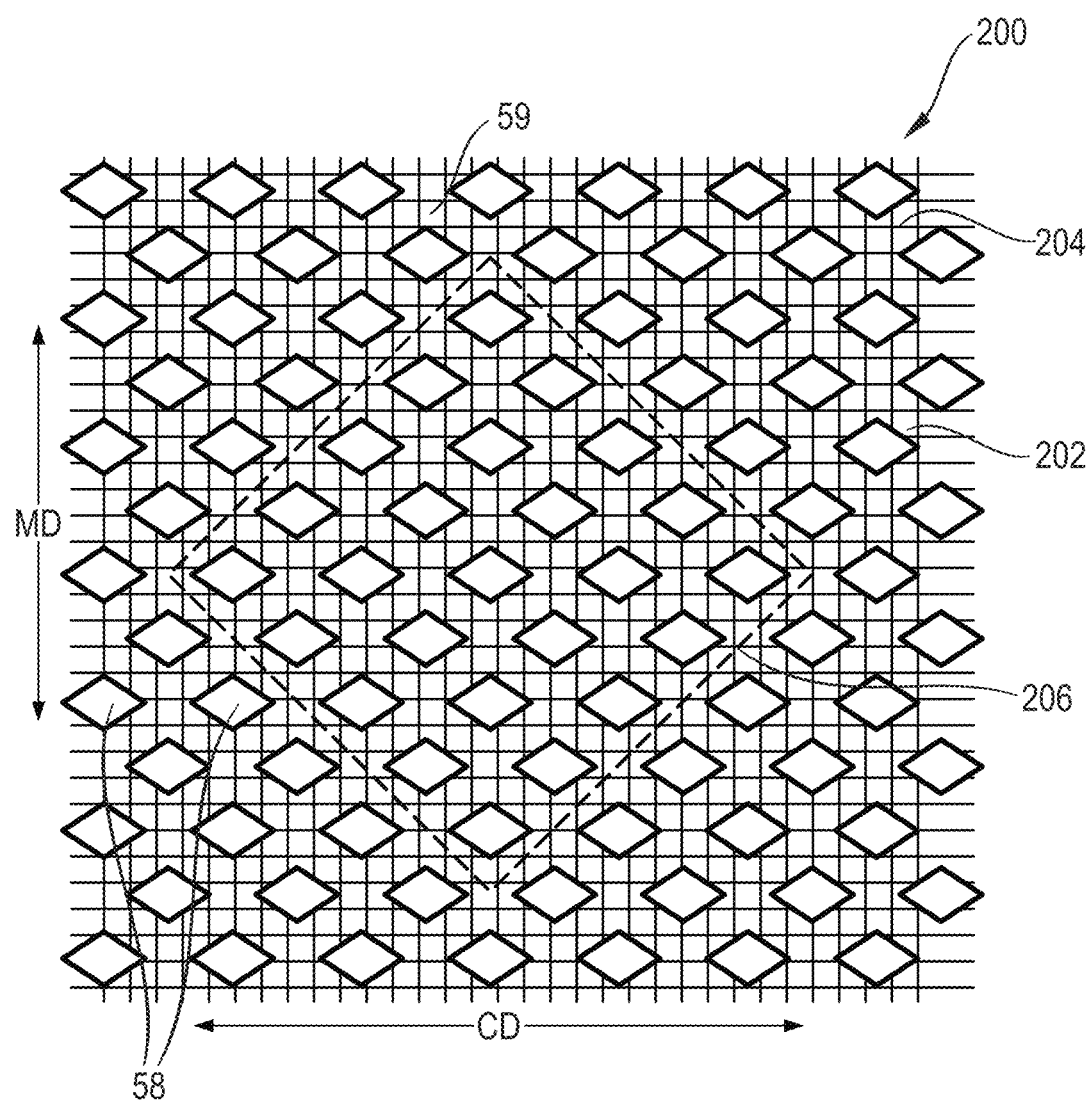
FIG. 11 is an example plan view of a portion of a papermaking belt used to make a fibrous substrate of a distribution material in accordance with the present disclosure.

Referring to FIG. 11, a web of the fibrous substrate of the distribution material 54 may be made through the use of a patterned papermaking belt 200 for forming three-dimensionally structured wet-laid and wet-formed webs as described in U.S. Pat. No. 4,637,859, issued Jan. 20, 1987, to Trokhan. The papermaking belt 200 may comprise a reinforcing element 202 (such as a woven belt) which may be coated with an uncured liquid photosensitive polymeric resin to a preselected thickness. A film (as illustrated in example form in FIG. 12) incorporating a desired resin pattern may be juxtaposed on the liquid photosensitive resin. Note that the film of FIG. 12 would form ovate raised resin portions on the reinforcing element 202. The resin may then be exposed to light of an appropriate wave length, such as an ultraviolet wave length, through the film. This exposure to light causes curing of the resin in the exposed areas (i.e., white portions, clear portions, or non-printed portions in the film). Unexposed (and uncured) resin (under the black portions or printed portions of the film) is removed from the belt 200 by fluid flushing leaving behind the cured resin (e.g., elements 58 of FIG. 11) forming the desired pattern, which pattern then is used to form, during the wet-forming phase of papermaking, a fibrous substrate web of the present disclosure. Because the pattern is transferred to the fibrous substrate web while the web is still at least partially wet and then the web is subsequently dried (to set the pattern), the three-dimensional elements (e.g., continuous network region and plurality of discrete zones) formed in the fibrous substrate are locked by the setting associated with drying. Furthermore, the web comprises one or more wet strength resins, such as Kymene, which functions to help lock the three-dimensional structure into the web via crosslinking. Thus, the three-dimensional elements of the web withstand losing their structure upon subsequent wetting by liquid bodily exudates and wearer induced strains and/or after receiving more than one liquid bodily exudate insults.

The fibrous substrate 55 may be formed using the patterned papermaking belt 200 having the plurality of raised resin portions 58, each raised resin portion 58 forming a corresponding (high density) discrete element 124 in the fibrous substrate. The areas of the papermaking belt 200 that do not have the raised resin portions 58 form the continuous network region (low density) in the fibrous substrate. In the alternative, the raised resin portions may form a continuous network on the papermaking belt 200, which would correspondingly form a high density continuous network region in the fibrous substrate, while the areas on the papermaking belt not having the raised resin portions would form the low density discrete elements in the fibrous substrate (not illustrated).

Figure 12:
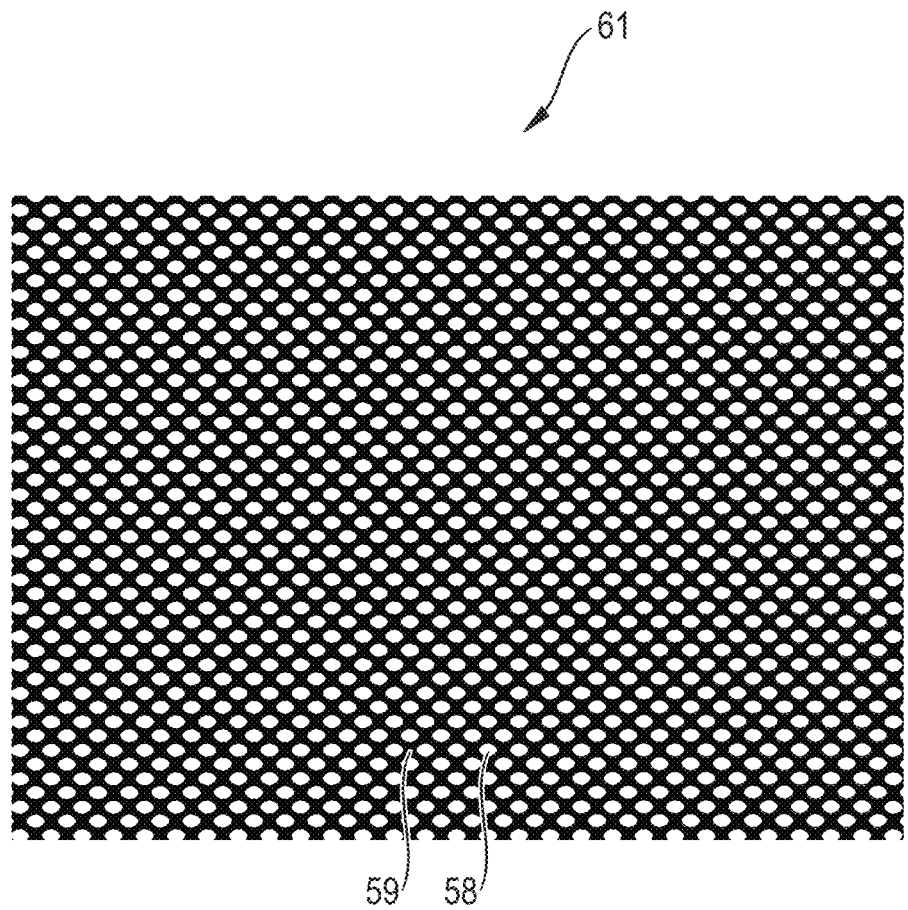
FIG. 12 is an example of a patterned film used in the process of creating a papermaking belt in accordance with the present disclosure.

Referring to FIGS. 11 and 12, each raised resin portion 58 of the papermaking belt 200 may be surrounded by a substantially continuous or continuous deflection conduit 59, created when uncured resin is removed from the papermaking belt 200. The deflection conduit 59 is formed under black, printed and/or non-light penetrating portions of the film applied to the resin before resin curing. An example patterned film 61 used for curing select portions of the resin on the papermaking belt 200 is illustrated in FIG. 12. Portions of the patterned film 61 that are black, printed, and/or non-light penetrating represent portions of the patterned papermaking belt 200 that are resin free or substantially resin free after resin curing, while portions of the patterned film 61 that are white, clear, non-printed, and/or light penetrating represent portions of the patterned papermaking belt 200 that have cured resin forming the raised resin elements 58.

Figure 13:
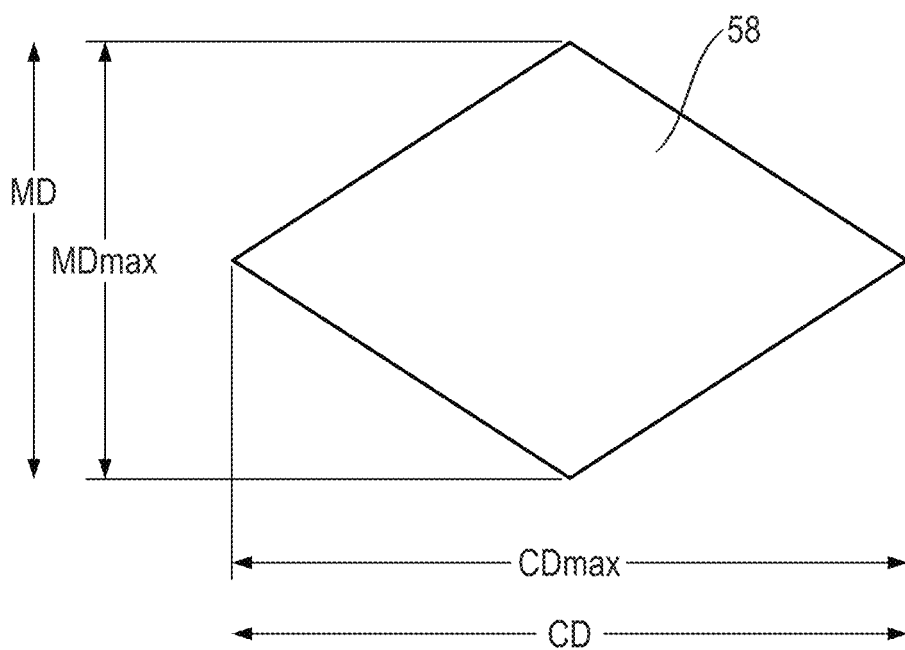
FIG. 13 is an example of a raised resin portion of a papermaking belt in accordance with the present disclosure.

Referring again to FIG. 11, one unit 206 (shown by dashed line) of one example of a pattern of the papermaking belt 200 is illustrated. Referring to FIG. 13, a top view of an individual raised resin portion 58 that forms an individual discrete element (high density in the fibrous substrate 55 is illustrated separate from the papermaking belt 200 for clarity. The raised resin portion 58 may have any suitable shape, such as a generally elongated shape having a major axis, CDmax, and a minor axis, MDmax. The raised resin portion 58 may also have any other suitable shape, such as round, ovate, square, rectangular, trapezoidal, or any other polygonal shape. As shown in the example of FIG. 13, individual raised resin portions 58 may have a rhomboid shape. One papermaking belt 200 may have more than one shape of raised resin portions. In general, the dimensions of the discrete elements 57 of the fibrous substrates 55 are determined by the dimensions of the corresponding raised portions 58 that they are formed on. That is, the fibrous substrate web is generally formed over the three-dimensional structure of the papermaking belt 200, so that in one sense the fibers are formed over, or molded to, the raised resin portions 58. If the raised resin portions form a continuous network, then the continuous network in the fibrous substrate web may be formed on the raised resin portions, while the discrete elements will be formed in deflection conduits intermediate portions of the raised resin portions. Although referred to herein, as "raised resin portions", it is also within the scope of the present disclosure to use materials other than resin to form the raised portions on the papermaking belt in various processes with or without the film 61. Those processes are also within the scope of the present disclosure, if they are able to form the fibrous substrates discussed herein.

In the raised resin portion 58 of FIG. 13, the ratio of the length of axis, CDmax, to the length of axis, MDmax, may be greater than or equal to one or less than 1. Stated another way, the axis, CDmax, may be longer than, shorter than, or may have the same length as the axis, MDmax. In one form, the ratio of the length of the axis, CDmax, to the length of the axis, MDmax, may be in the range of 1 to about 3 or in the range of 1 to about 4 or more.

In one form, the CDmax of one raised resin portion 58 may be between about 1.50 mm to about 3.50 mm, about 1.55 mm to about 2.00 mm, or about 1.53 mm and about 2.29 mm, and the MDmax of one raised portion 58 may be between about 0.80 mm to about 2.00 mm, about 1.00 mm to about 1.70 mm, or about 1.01 mm to about 1.53 mm, specifically reciting al 0.01 mm increments within the above-specified ranges and all ranges formed therein or thereby.

Any other suitable dimensions of the raised portions or raised resin portions are within the scope of the present disclosure, depending on the pattern desired for the fibrous substrate.

Some example shapes of the discrete zones (formed by the raised portions or raised resin portions) may comprise circles, ovals, squares, rectangles, ellipses, and polygons having any suitable number of sides. There is no requirement that the discrete zones be regular polygons or that the sides of the discrete zones 124 be straight. Instead, the discrete zones may comprise curved sides, stepped sides, or other multi-level sides.

Process of Making a Web of the Three-Dimensional Fibrous Substrates

Figure 14:
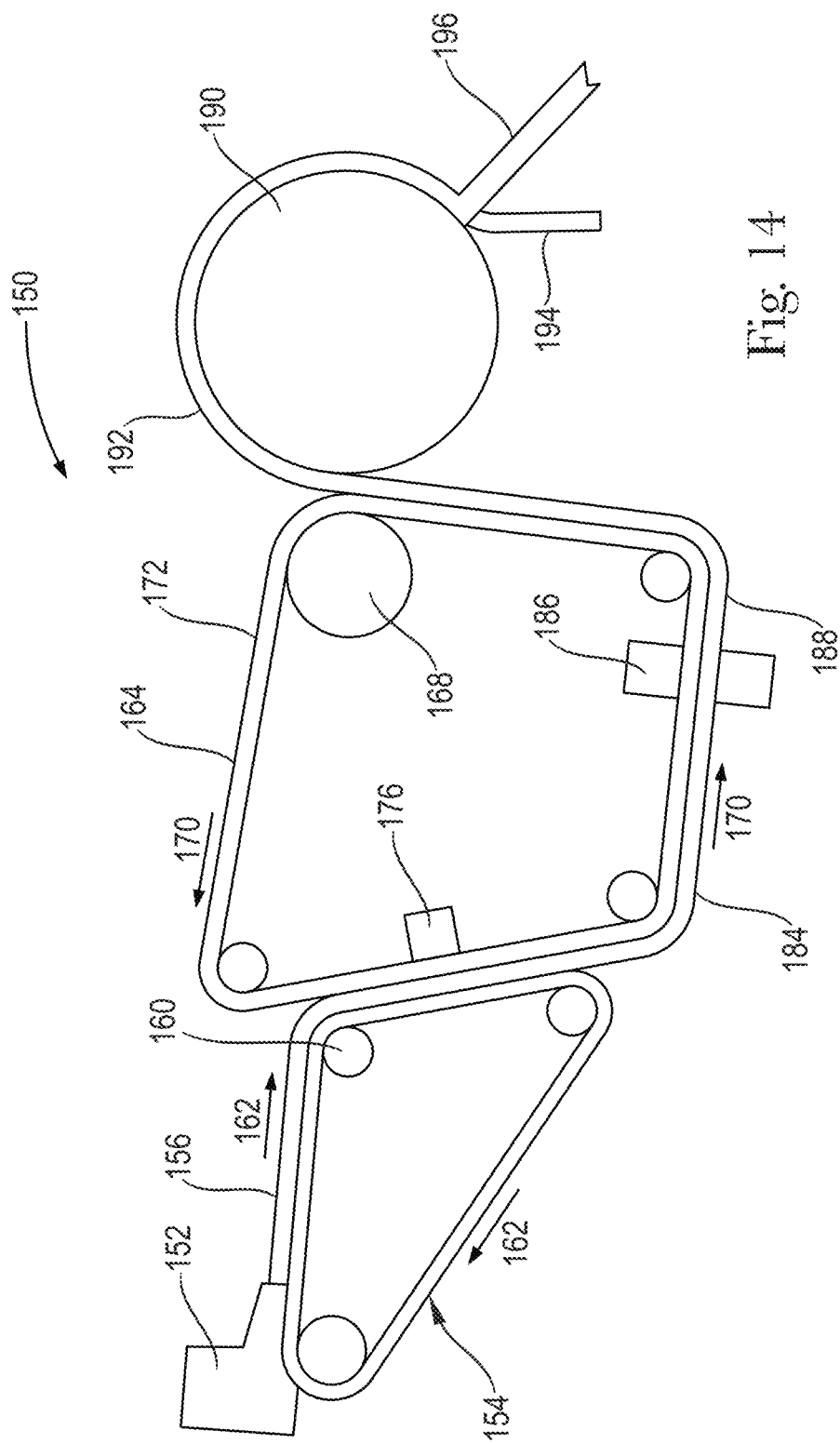
FIG. 14 is an example of a fibrous substrate production process in accordance with the present disclosure.

FIG. 14 is a simplified, schematic representation of one example of a continuous fibrous substrate web making process and machine.

The example process, represented as 150, for making a continuous web of the fibrous substrates of the distribution material of the present disclosure comprises supplying an aqueous dispersion of fibers to a headbox 152. From the headbox 152, the aqueous dispersion of fibers may be delivered to a foraminous member 154 to produce an embryonic fibrous web 156. The foraminous member 154 may be conveyed in the direction indicated by arrow 162 by any suitable drive mechanism, such as a motor, for example (not illustrated).

After the aqueous dispersion of fibers is deposited onto the foraminous member 154, the embryonic fibrous web 156 is formed, typically by the removal of a portion of the aqueous dispersing medium by techniques known to those skilled in the art. The embryonic fibrous web 156 may then travel with the foraminous member 154 about return roll 160 and may be brought into contact with a papermaking belt 164. While in contact with the papermaking belt 164, the embryonic fibrous web 156 (and fibers thereof) may be deflected, rearranged, and/or further dewatered. The papermaking belt 164 may be similar to the papermaking belt 200 discussed herein.

The papermaking belt 164 may be in the form of an endless belt that can travel in the direction indicated by directional arrow 170. The papermaking belt 164 may be constructed in such a manner that when water is caused to be removed from the embryonic fibrous web 156, as by the application of differential fluid pressure, such as by a vacuum box 176, and when the water is removed from the embryonic fibrous web 156 in the direction of the papermaking belt 164, the water can be discharged from the system without having to again contact the embryonic fibrous web 156 in either the liquid or the vapor state. A first surface 172 of the papermaking belt 164 may comprise one or more raised resin portions 58, as described herein. The raised portions may be discrete elements or form network regions.

After the embryonic fibrous web 156 has been associated with the papermaking belt 164, wet-laid fibers within the embryonic fibrous web 156 are deflected into the deflection conduits (or other non-resin or raised material containing areas on the papermaking belt, such as discrete zones) present in the papermaking belt member 164 to lead to an intermediate fibrous web 184.

The intermediate fibrous web 184 may first pass through an optional predryer 186. The predryer 186 may be a conventional flow-through dryer (hot air dryer) known to those of skill in the art. The predried fibrous web 188 may travel to an impression nip roll 168. As the predried fibrous web 188 passes through the nip formed between impression nip roll 168 and a surface of a Yankee dryer 190, the pattern formed by the top surface 172 of the papermaking belt 164 is impressed into the predried fibrous web 188 to form a pattern of raised areas in the fibrous web 192. The raised areas (whether network regions or discrete zones) are formed in areas of the imprinted fibrous web 192 where little or no resin was present on the papermaking belt 164. The raised areas are the low density areas of the imprinted fibrous web 192. High density areas (whether network regions or discrete zones) are formed in the imprinted fibrous web 192 where the resin or other material was present on the papermaking belt 164.

The imprinted fibrous web 192 may then be foreshortened by creping the web 192 with a creping blade 194 (or doctor blade) to remove the web 192 from the surface of the Yankee dryer 190 resulting in the production of a creped fibrous substrate web 196. The fibrous substrate web 196 may be wound in a roll for later use in the manufacture of a distribution material or fed directly into a process for making the distribution material.

In other instances, the fibrous substrate 55 may be uncreped. Some techniques used to produce uncreped fibrous substrates are taught in, for example, European Patent Application 0 677 612 A2, published on Oct. 18, 1995, to Wendt, et al., European Patent Application 0 617 164 A1, published on Sep. 28, 1994, to Hyland et al., and U.S. Pat. No. 5,656,132, issued on Aug. 12, 1997, to Farrington et al.

In an instance where the fibrous substrate web 196 is later used, the fibrous substrate web may be unwound from the roll and cut into a plurality of appropriately sheets of fibrous substrates. The fibrous substrate web may also be used to form a portion or all of a continuous distribution material and then the continuous distribution material may be cut into a plurality of appropriately sized sheets. The distribution material 54 may comprise one or more layers of the fibrous substrate 55. If the distribution material 54 contains more than one layer of the fibrous substrate, the layers may be stacked in a facing relationship to each other. Although in a facing relationship, one layer may be slightly staggered (CD and/or MD) relative to another layer in some instances. In other instances, a piece of the fibrous substrate may be cut from the fibrous substrate web 196 large enough so that it can be folded over itself at least partially, one full time, or more than one time (e.g., one fibrous substrate folded twice over itself).

Construction of the Distribution Material

Referring again to FIG. 1, one or more of the front region 541, back region 542, and/or the middle region 543 of the distribution material 54 may comprise one or more layers of the fibrous substrate, two or more layers of the fibrous substrate, three or more layers of the fibrous substrate, from 1 to 15 layers of the fibrous substrate, from 1 to 10 layers of the fibrous substrate, from 1 to 5 layers of the fibrous substrate, or from 2 to 5 layers of the fibrous substrate. One or more of the regions 541, 542, and 543 may have the same number of layers of the fibrous substrate or a different number of layers of the fibrous substrate. In one instance, one or more of the regions may have more or less layers than the remaining regions.

The distribution material may have any suitable longitudinal or lateral width depending on the size of the absorbent article into which it is incorporated.

Each layer of the fibrous substrate of the distribution material 54 may have different sizes such as different longitudinal and/or lateral dimensions. Incorporating layers of fibrous substrates with different sizes may enable profiling the basis weight and total dry caliper of the distribution material 54 at certain locations of the absorbent article 20.

FIGS. 15A-15G show cross-sectional views of various example distribution layers, or portions thereof, of the present disclosure.

Figure 15A:
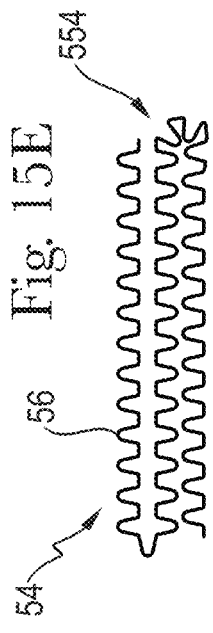
FIGS. 15A-15G illustrate example cross-sectional views of distribution materials, or portions of distribution materials, in accordance with the present disclosure.

FIG. 15A shows an example of a distribution material 54 comprising three individual layers of fibrous substrates. Each layer of the fibrous substrate may comprise a pattern of raised elements 56. The distribution material 54 may include void spaces due to the pattern of the raised elements 56, the spaces between the different layers of the fibrous substrate of the distribution material 54, and the porosity of each fibrous substrate. By providing more than one layer of fibrous substrates in the distribution material 54, void spaces may be formed. These void spaces may help more quickly drain liquid bodily exudates from the topsheet 24 and distribute and transfer them to the absorbent core 28.

The longitudinal and lateral center of the distribution materials disclosed herein may be positioned in a location of the absorbent article 20 which may coincide with, or be positioned proximal to, a pee point of the wearer, a menses discharger point on the wearer, or a BM discharge point on the wearer.

A distribution material made of unconsolidated air-laid fibers may form some cracks and disruptions especially when insulted with liquid bodily exudates and undergoes strain caused by the wearer's movement. These disruptions are mainly due to the fact that the unconsolidated air-laid fibers may not be able to provide enough wet integrity. As a result, undesired randomly positioned liquid channels in the distribution material 54 may occur and be observed as distribution material tears or separations. The liquid bodily exudates may be routed through these liquid channels directly to the absorbent core 28. As a consequence, the liquid bodily exudates may not be efficiently distributed in the distribution material if unconsolidated air-laid fibers are used. Moreover, these uncontrolled disruptions may be perceived as sign of lower product quality from some consumers.

In the case of the present disclosure, where a distribution material comprises one or more layers of fibrous substrates comprising wet-laid or wet-formed fibers, the distribution material may have an improved cohesive structure or wet strength compared to the unconsolidated air-laid fibers discussed above. Due to the wet-laid and wet-formed papermaking process as described herein, the wet-laid and wet-formed fibers relatively strongly adhere to each other. The fibrous substrate(s) of the distribution material of the present disclosure is/are thus less prone to form disruptions when wetted by liquid bodily exudates. Hence, the distribution material, of the present disclosure, comprising one or more layers of fibrous substrates has an improved wet integrity relative to unconsolidated air-laid fibers. Liquid bodily exudates are therefore more efficiently distributed in the distribution material before being transferred to the absorbent core 28. Furthermore, due to the papermaking process as described herein, the wet-laid and wet-formed fibrous substrates of the present disclosure better retain their three-dimensional structure, not only upon liquid bodily exudate wetting, but also upon wearer induced strains. This is the due to the fact that the fibrous substrates are wet molded (i.e., wet-formed) and then dried to set the three-dimensional structure in addition to the provision of one or more wet strength resins.

Referring again to FIG. 15A, the raised elements 56 of the fibrous substrate may protrude toward the topsheet 24 (and/or the acquisition layer) and/or toward the absorbent core 28. In all of the example forms of FIGS. 15A-15G, the layer of the fibrous substrate closest to the top of the page is closest to the topsheet and the layer of the fibrous substrate closest to the bottom of the page is closest to the absorbent core. Forms of FIGS. 15A-15G that are inverted, however, are also within the scope of the present disclosure.

One or more of the layers of the fibrous substrates of the distribution material 54 may have a three-dimensional structure. The three-dimensional structure, which results from the wet-laid and wet formed papermaking process, may reinforce the wet integrity of the fibrous substrates. The cohesive structure of the distribution material 54 may be due to how the wet-laid fibers adhere to each other and also due to the three-dimensional structure of each fibrous substrate. The cohesive structure may provide a much more compact distribution material 54 than a distribution material made of unconsolidated air-laid fibers, which may provide a comfort and thinnest benefit to an absorbent article containing the distribution materials of the present disclosure.

In contrast with a distribution material made of unconsolidated air-laid fibers, the distribution material 54 of the present disclosure may be specially designed to provide one or more visual features. For example, the distribution material 54 may comprise printing, graphics, and/or colors in at least portions thereof. Having a distribution material comprising one or more visual features may provide one or more visual signals to the caregiver from the wearer-facing surface of the absorbent article that may help indicate the remaining absorbent capacity of the absorbent article, for example. The one or more visual features may also provide one or more visual signals that may be configured to aid the consumer to in selecting an appropriate absorbent article for an appropriate time (e.g., daytime wear, nighttime wear).

In addition to or instead of providing the distribution material with one or more visual features, the distribution material, or portions thereof, may be embossed, by providing discrete embossed points that are typically circular or ovate. Embossing the distribution material may help improving the depth perception of the absorbent article when viewing the absorbent article from the wearer-facing surface thereof.

Figure 15B:
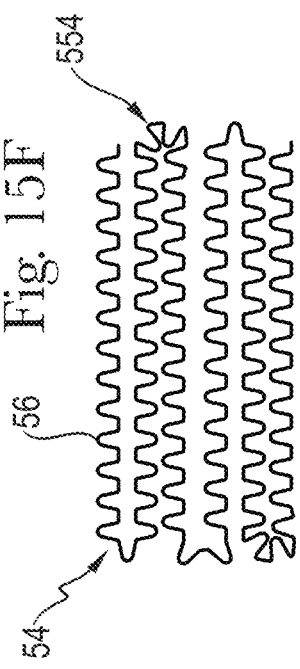

The one or more layers of the fibrous substrates of the distribution material 54 in any of the various regions, or portions thereof, may be at least partially folded over themselves to form two or more layers in the distribution material. FIG. 15B illustrates a first sheet 552 of a fibrous substrate which has been trifolded to form three layers and placed on top of a non-folded second sheet 551.

Figure 15C:
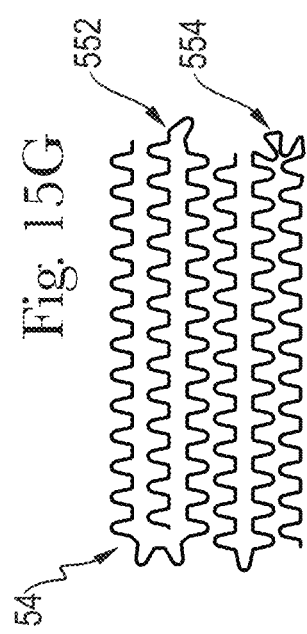
Figure 15D:

FIGS. 15C and 15D, respectively, illustrate examples of a distribution material 54 which comprises a single sheet 552 folded over itself to form a distribution material, or a portion thereof, that has either 3 layers of the fibrous substrates (FIG. 15C) or 5 layers of the fibrous substrate (FIG. 15D).

In an instance, where the sheet 552 is folded at least partially over itself twice, the longitudinal side edges of the distribution material 54 may have increased stiffness. This feature may be desirable to provide stiffer longitudinal side edges and softer portions in the middle of the distribution material. In other forms, the longitudinal side edges of the distribution material may be incrementally stretched, slitted, and/or cut to reduce their stiffness.

Figure 15E:
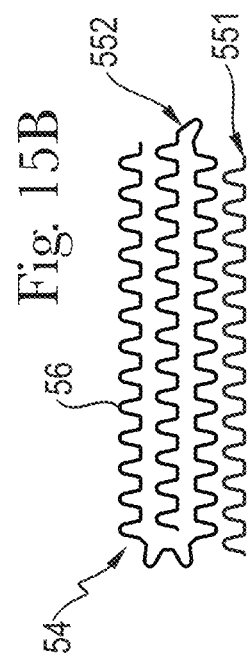
Figure 15F:
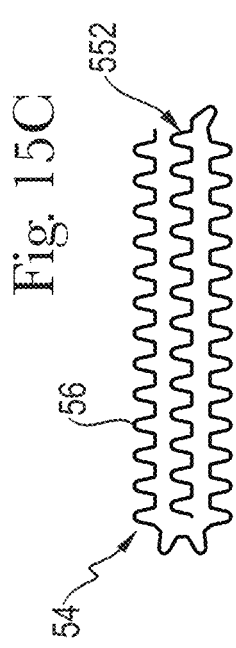
Figure 15G:
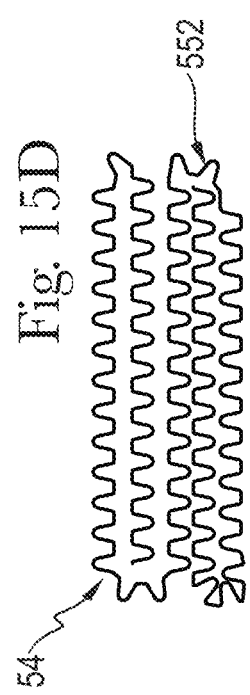

The distribution material may comprise at least one sheet of the fibrous substrate which is S-folded to form a plurality of layers of the fibrous substrate. FIG. 15E illustrates an example of a sheet 554 of the fibrous substrate which has been S-folded to form 3 layers of the fibrous substrate. FIG. 15F illustrates an example of a sheet 554 of the fibrous substrate which has been S-folded to form 6 layers of the fibrous substrate. FIG. 15G illustrates an example of a distribution material 54 comprising a sheet 554 of the fibrous substrate which has been S-folded to form 3 layers of the fibrous substrate. The sheet 554 is placed below a sheet 552 of the fibrous substrate which has been trifolded. Other forms of the fibrous substrates of the distribution material recognized by those of skill in the art are also within the scope of the present disclosure.

The outer perimeter of the distribution material 54 may have different geometries, such as rectangular, ovate, square, a so-called "dog bone" shape, or a so-called "hour-glass" shape, which shows a tapering along its width at least in a crotch region of the absorbent article 20. Other outer perimeter geometries are also within the scope of the present disclosure.

The distribution material 54 may comprise one or more layers of the fibrous substrates, each layer having a length L1 and a width W1. One or more of the layers of the fibrous substrates may comprise one or more slits 124 across the width direction W1 to create at least a first, second and central subsections 121, 122 and 123, as shown as an example in FIG. 16A. Each subsection may be folded toward the longitudinal axis of the distribution material 54. For example, FIG. 16B shows that the central subsection 123 has been folded while the first and second subsections 121 and 122 remain unfolded. In other forms, the first and second subsections 121 and 122 may also be folded and the central subsection 123 may or may not be folded.

The central subsection 123 of FIGS. 16A and 16B may coincide with the middle region 543 of the distribution material 54. Alternatively, the central subsection 123 may be longitudinally longer or shorter than the middle region 543 of the distribution material 54.

A top portion of the distribution material 54 may be attached to the topsheet 24 or to any layer, e.g. the acquisition layer 52, which is positioned between the topsheet 24 and the distribution material 54. A bottom portion of the distribution material 54 may be attached to a wearer-facing portion or substrate of the absorbent core 28 or to any layer between the distribution material 54 and the wearer-facing portion of the absorbent core 28. In other forms, the distribution material 54 may not be attached to any of the above-described layers and may merely be positioned therebetween without actual attachment (e.g., no gluing, bonding etc.).

In one form, the top portion of the distribution material 54 may be attached to the topsheet 24 or to any layer between the topsheet 24 and the distribution material 54 by a patterned adhesive. The patterned adhesive may comprise one or more colors. The bottom portion of the distribution material 54 may be attached to a portion or substrate of the absorbent core 28 facing the topsheet 24 or to any layer between the portion or the substrate of the absorbent core 28 facing the topsheet 24 and the distribution material 54 by the same or a different patterned adhesive.

The patterned adhesive may comprise a plurality of adhesive lines that are continuous or discontinuous, linear or non-linear. The lines may extend in any suitable direction, such as longitudinally or laterally, for example.

In one instance, the patterned adhesive may be a plurality of overlapping, substantially continuous, semi-cycloidal lines of adhesive extending along the longitudinal direction, lateral direction, or other direction of the absorbent article 20.

In other instances, the patterned adhesive may be a plurality of separate lines, such as straight lines, spirals, and/or may be a plurality of dots of adhesive.

If the adhesive is hydrophobic (e.g., some hotmelt adhesives), the liquid bodily exudates may be drained from the distribution material 54 to the absorbent core 28 between the patterned adhesive.

Each substrate of the distribution material 54 may be attached to each adjacent substrate of the distribution material with a similar patterned adhesive, as set out above.

Sanitary Napkin

Referring to FIG. 17, the absorbent articles described herein may be a sanitary napkin 3010. The sanitary napkin 3010 may comprise a liquid permeable topsheet 3014, a liquid impermeable, or substantially liquid impermeable, backsheet 3016, and an absorbent core 3018. The absorbent core 3018 may have any or all of the features described herein. The sanitary napkin may comprise a secondary topsheet 3019. Either in addition to or in lieu of the second topsheet 3019, the sanitary napkin may comprise one or more of the distribution materials of the present disclosure. The distribution materials may comprise one or more three-dimensional fibrous substrates of the present disclosure having any suitable features appropriate for a sanitary napkin. The distribution material(s) may be positioned intermediate the topsheet 3014 and the absorbent core 3018, the secondary topsheet 3019 and the topsheet 3014, the secondary topsheet 3019 and the absorbent core 3018, the absorbent core 3018 and the backsheet 3016, and/or any of the named components and other layer or material of a sanitary napkin. The sanitary napkin 3010 may also comprise wings 3020 extending outwardly with respect to a longitudinal axis 3080 of the sanitary napkin 3010. The sanitary napkin 3010 may also comprise a lateral axis 3090. The wings 3020 may be joined to the topsheet 3014, the backsheet 3016, and/or the absorbent core 3018. The sanitary napkin 3010 may also comprise a front edge 3022, a rear edge 3024 longitudinally opposing the front edge 3022, a first side edge 3026, and a second side edge 3028 longitudinally opposing the first side edge 3026. The longitudinal axis 3080 may extend from a midpoint of the front edge 3022 to a midpoint of the rear edge 3024. The lateral axis 3090 may extend from a midpoint of the first side edge 3028 to a midpoint of the second side edge 3028. The sanitary napkin 3010 may also be provided with additional features commonly found in sanitary napkins as is known in the art.

Packages

Absorbent articles comprising the distribution materials of the present disclosure may be placed into packages. The packages may comprise polymeric films and/or other materials. Graphics or indicia relating to properties of the absorbent articles may be formed on, positioned on, and/or placed on outer portions of the packages. Each package may comprise one or more absorbent articles. The absorbent articles may be packed under compression so as to reduce the size or height of the packages while still providing an adequate amount of absorbent articles per package.

Accordingly, packages of the absorbent articles according to the present disclosure may have an in-bag stack height of less than about 80 mm, less than about 78 mm, or less than about 76 mm, according to the In-Bag Stack Height Test described herein. Alternatively, packages of the absorbent articles of the present disclosure may have an in-bag stack height of from about 72 mm to about 80 mm or from about 74 mm to about 78 mm, specifically reciting all 0.5 mm increments within the specified ranges and all ranges formed therein or thereby, according to the In-Back Stack Height Test described herein. Further details regarding in-back stack height are disclosed in U.S. Pat. No. 8,585,666, to Weisman et al., issued on Nov. 19, 2013.

Basis Weight

One or more fibrous substrates of the distribution material 54 may have a basis weight in the range of about 5 gsm to about 150 gsm, about 10 gsm to about 100 gsm, about 10 gsm to about 60 gsm, about 10 gsm to about 50 gsm, or about 15 gsm to about 50 gsm, specifically reciting all 1 gsm increments within the above-specified ranges and all ranges formed therein or thereby, according to the Basis Weight Test herein.

Dry Caliper

A fibrous substrate of the distribution material 54 may have a Dry caliper at a pressure of 2.06 kPa from about 0.1 mm to about 2.0 mm, specifically reciting all 0.01 mm increments within the specified range and all ranges formed therein, according to the Dry Caliper Test Method herein.

Total Dry Caliper

The distribution material 54 may have a Total Dry caliper at a pressure of 2.06 kPa from about 0.1 mm to about 30.0 mm, specifically reciting all 0.1 mm increments within the above-specified range and all ranges formed therein, according to the Dry Caliper Test Method herein.

Wet Burst Strength

A fibrous substrate of the distribution material 54 may have a Wet Burst Strength from about 50 g to about 500 g, from about 250 g to about 350 g, from about 275 g to about 325 g, or from about 300 g to about 350 g, specifically reciting all 1 g increments within the specified ranges and all ranges formed therein or thereby, according to the Wet Burst Strength Test Method herein.

Total Dry Tensile Strength

Fibrous substrates of the distribution material 54 may have a Total Dry Tensile Strength from about 1,000 g/in to about 3,000 g/in, from about 1,500 g/in to about 2,500 g/in, from about 1,700 g/in to about 2,200 g/in, from about 1,800 g/in to about 2,000 g/in, specifically reciting all 1 g/in increments within the specified ranges and all ranges formed therein or thereby, according to the Tensile Test Method herein.

Geometric Mean TEA (Tensile Energy Absorption)

A fibrous substrate of the distribution material 54 may have a Geometric Mean TEA of about 100 g*in/in$^2$ to about 500 g*in/in$^2$, specifically reciting all 1 g*in/in$^2$ increments within the specified range and all ranges formed therein or thereby, about 100 g*in/in$^2$ or more, about 150 g*in/in$^2$ or more, about 200 g*in/in$^2$ or more, or about 300 g*in/in$^2$ or more according to the Tensile Test Method described herein.

Geometric Mean Tensile Strength

A fibrous substrate of the distribution material 54 may have a Geometric Mean Tensile Strength of about 200 g/in to about 1,300 g/in, of about 700 g/in to about 1,100 g/in, or of about 800 g/in to about 1,000 g/in, specifically reciting all 1 Win increments within the specified ranges and all ranges formed therein or thereby, about 500 g/in or more, about 600 g/in or more, about 700 g/in or more, or about 800 g/in or more, according to the Tensile Test Method described herein.

Geometric Mean Modulus

A fibrous substrate of the distribution material 54 may have a Geometric Mean Modulus of about 500 g/cm to about 5,000 g/cm, of about 650 g/cm to about 3,800 g/cm, of about 1,000 g/cm to about 3,000 g/cm, of about 1,500 g/cm to about 2,500 g/cm, of about 1,900 g/cm to about 2,300 g/cm, or of about 2,000 g/cm to about 2,200 g/cm, specifically reciting all 1 g/cm increments within the specified ranges and all ranges formed therein or thereby, about 5,000 g/cm or less, about 4,000 g/cm or less, about 3,000 g/cm or less, about 2,500 g/cm or less, or about 2,200 g/cm or less, according to the Tensile Test Method described herein.

Geometric Mean Peak Elongation

A fibrous substrate of the distribution material 54 may have a Geometric Mean Peak Elongation of about 5% to about 30%, of about 10% to about 23%, of about 12% to about 16%, of about 13% to about 15%, specifically reciting all 1% increments within the specified ranges and all ranges formed therein or thereby, of about 5% or greater, of about 8% or greater, of about 10% or greater, of about 12% or greater, or of about 13% or greater, according to the Tensile Test Method described herein.

Elevation

Suitable fibrous substrates having a network region and a plurality of discrete zones may have predetermined elevations. For example, one of the network regions or the discrete zones may have an elevation from about 50 microns to about 5,000 microns, from about 100 microns to about 2,000 microns, or from about 150 microns to about 1,500 microns, specifically reciting all 1 micron increments within the specified range and all ranges formed therein or thereby, according to the Topographic Measurements of Differential Density Fibrous Substrates Test described herein.

Test Methods

Unless otherwise specified, all tests described herein are conducted on samples that have been conditioned at a temperature of 23° C.±1C.° and a relative humidity of 50%±2% for a minimum of 2 hours prior to testing. All tests are conducted under the same environmental conditions. Do not test samples that have defects such as wrinkles, tears, holes, and like. Samples conditioned as described herein are considered dry samples. Further, all tests are conducted in such conditioned room.

To obtain a sample of the distribution material, use the following steps:
(1) Lay the absorbent article on a flat work surface and tape it down flat, elastics in a stretched state, wearer-facing surface facing the tester;
(2) Remove the topsheet around a perimeter of the distribution material using a razor blade and cryogenic spray (if needed);
(3) Remove any other layers intermediate the topsheet and the distribution material using a razor blade and cryogenic spray (if needed);
(4) Once the distribution material is exposed, use the cryogenic spray to remove it from the diaper;
(5) Allow the sample to equilibrate at 23±2° C. and 50±5% relative humidity for 24 hours prior to testing; and
(6) Specimens that are appropriately sized for a particular test (within the knowledge of those of skill in the art) are cut from the distribution material.

Wet Burst Strength Test Method

The wet burst strength as used herein is a measure of the ability of a fibrous substrate of a distribution layer to absorb energy, when wet and subjected to deformation with regard to the plane of the fibrous substrate.

The wet burst strength of a fibrous substrate (referred to as "sample" within this test method) is determined using an electronic burst tester and specified test conditions. The results obtained are averaged out of 4 replicates and the wet burst strength is reported for a fibrous substrate consisting of a single layer of wet-laid fibers.

Equipment
  Apparatus: Burst Tester—Thwing-Albert Vantage Burst Tester or equivalent ball burst instrument where the ball moves downward during testing. Refer to manufacturer's operation and set-up instructions. The ball diameter is 1.59 cm and the clamp opening diameter is 8.9 cm.
  Calibration Weights—Refer to manufacturer's calibration instructions
  Conditioned Room Temperature and Humidity controlled within the following limits for
Laboratory Testing:
  Paper Cutter—Cutting board, 600 mm size
  Scissors—100 mm, or larger
  Pan—Approximate Width/Length/Depth: 240×300×50 mm, or equivalent
  Distilled water at the temperature of the conditioned room used Sample Preparation Cut the samples so that they are 228 mm in length and width of 140 mm in width.

Operation

Set-up and calibrate the Burst Tester instrument according to the manufacturer's instructions for the instrument being used.

Holding the sample by the narrow edges, the center of the sample is dipped into a pan filled approximately 25 mm from the top with distilled water. The sample is left in the water for 4 (±0.5) seconds.

The excess water is drained from the sample for 3 (±0.5) seconds holding the sample in a vertical position.

The test should proceed immediately after the drain step. The sample should have no perforations, tears or imperfections in the area of the sample to be tested. If it does, start the test over.

The sample is placed between the upper and lower rings of the Burst Tester instrument. The sample is positioned centered and flat on the lower ring of the sample holding device in a manner such that no slack in the sample is present.

The upper ring of the pneumatic holding device is lowered to secure the sample.

The test is started. The test is over at sample failure (rupture) i.e., when the load falls 20 g from the peak force. The maximum force value is recorded.

The plunger will automatically reverse and return to its original starting position.

The upper ring is raised in order to remove and discard the tested sample.

The procedure is repeated until all 4 replicates have been tested.

Calculation $$\text{Wet Burst Strength} = \text{sum of peak load readings/number of replicates tested}$$

Report the Wet Burst results to the nearest gram.

Basis Weight Test Method

Basis weight of a fibrous substrate is measured on stacks of twelve usable units using a top loading analytical balance with a resolution of ±0.001 g. The balance is protected from air drafts and other disturbances using a draft shield. A precision cutting die, measuring 3.500 in ±0.0035 in by 3.500 in ±0.0035 in is used to prepare all samples.

With a precision cutting die, cut the samples into squares. Combine the cut squares to form a stack twelve samples thick. Measure the mass of the sample stack and record the result to the nearest 0.001 g.

The Basis Weight is calculated in $lbs/3000\ ft^2$ or $g/m^2$ as follows:

$$\text{Basis Weight} = (\text{Mass of stack})/[(\text{Area of 1 square in stack}) \times (\text{Number of squares in stack})]$$

For example, $$\text{Basis Weight}(lbs/3000\ ft^2) = [[\text{Mass of stack}(g)/453.6\ (g/lbs)]/[12.25(in^2)/144\ (in^2/ft^2) \times 12]] \times 3000$$

or, $$\text{Basis Weight}(g/m^2) = \text{Mass of stack}(g)/[79.032(cm^2)/10,000(cm^2/m^2) \times 12]$$

Report result to the nearest $0.1\ lbs/3000\ ft^2$ or $0.1\ g/m^2$. Sample dimensions can be changed or varied using a similar precision cutter as mentioned above, so as at least 100 square inches of sample area in stack.

Average Density Test Method

Figure 18:
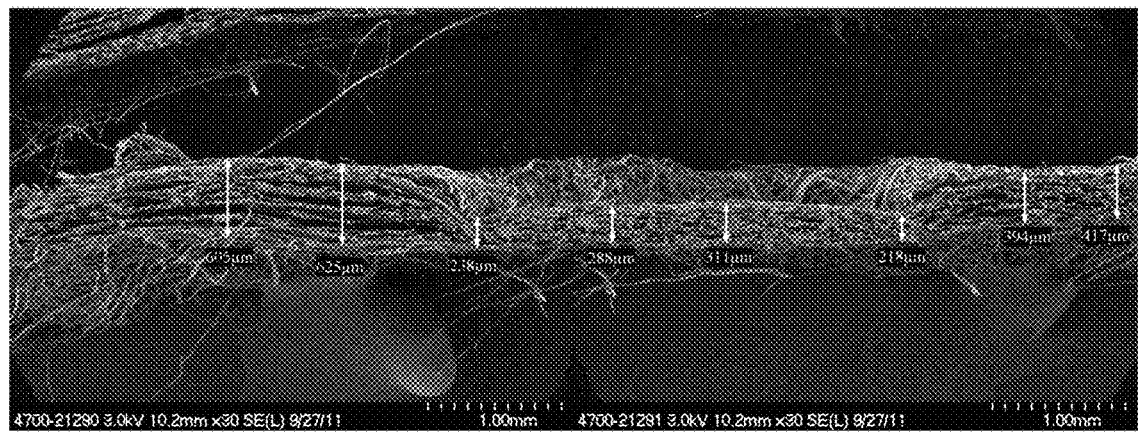
FIG. 18 is a cross-sectional view of a network region and a plurality of discrete zones of a fibrous substrate as shown using a SEM micrograph in accordance with the present disclosure.

Fibrous substrate can comprise network regions and pluralities of discrete zones which have characteristic densities. A cross-sectional, SEM micrograph of such a fibrous substrate is shown in FIG. 18. The regions of the fibrous substrate are illustrated in the micrograph by the zones comprising different caliper or thickness. These caliper differences are one of the factors responsible for the superior performance characteristics of these fibrous substrates.

The regions with higher caliper are lower in structure density and these are typically referred to as "pillows". The regions with lower caliper are higher in structure density and these are typically referred to as "knuckles."

The density of the regions within a fibrous substrate are measured by first cutting for a length of at least 2-3 knuckle and pillow regions with a previously unused single edge PTFE-treated razor blade such as the GEM® razor blades available from Ted Pella Inc. Only one cut is made per razor blade. Each cross-sectioned sample is mounted on a SEM sample holder, secured by carbon paste, then plunged and frozen in liquid nitrogen. The sample is transferred to an SEM chamber at −90° C., coated with Gold/Palladium for 60 seconds and analyzed using a commercially available SEM equipped with a cryo-system such as a Hitachi S-4700 with Alto cryo system and PCI (Passive Capture Imaging) software for image analysis or an equivalent SEM system and equivalent software. All samples are evaluated while frozen to ensure their original size and shape under vacuum while in the scanning electron microscope.

Pillow and knuckle thickness or network regions and discrete zone thickness are determined using image analysis software associated with the SEM equipment. As the measurements are the thickness of a sample, such analysis software is standard for all SEM equipment. Measurements are taken where the thickness of the region or zone are at their respective local maximum values. Thickness values for at least 2 individual, separate network regions and at least 2 individual, discrete zones are recorded and then averaged and reported as the average network region thickness and average discrete zone thickness, respectively. The average thicknesses are measured in units of microns.

Separately, the basis weight of the sample being measured for density is determined using the Basis Weight Test Method defined herein. The basis weight as measured in gsm (g/m$^2$) is calculated using the Basis Weight Test Method and used to calculate the region density.

Below is an example for calculating the average network density and average discrete zone density for a sample with a basis weight of 100 g/m$^2$, a network region average thickness of 625 micron, and a discrete zone average thickness of 311 micron.

$$\text{Average network density}\left(\frac{g}{cc}\right) =$$

$$\frac{\text{basis weight}}{\text{network thickness}} = \frac{100\frac{g}{m^2}}{625 \times 10^{-6}\ m} \times \frac{m^2}{1 \times 10^6\ cc} = 0.16 \frac{g}{cc}$$

$$\text{Average discrete zone density}\left(\frac{g}{cc}\right) =$$

$$\frac{\text{basis weight}}{\text{discrete zone thickness}} = \frac{100\frac{g}{m^2}}{311 \times 10^{-6}\ m} \times \frac{m^2}{1 \times 10^6\ cc} = 0.32 \frac{g}{cc}$$

Tensile Test Method: Elongation, Tensile Strength, TEA and Modulus

Elongation, Tensile Strength, TEA and Tangent Modulus are measured on a constant rate of extension tensile tester with computer interface (a suitable instrument is the EJA Vantage from the Thwing-Albert Instrument Co. Wet Berlin, N.J.) using a load cell for which the forces measured are within 10% to 90% of the limit of the cell. Both the movable (upper) and stationary (lower) pneumatic jaws are fitted with smooth stainless steel faced grips, 25.4 mm in height and wider than the width of the test specimen. An air pressure of about 60 psi is supplied to the jaws.

Eight usable units of fibrous substrate are divided into two stacks of four samples each. The samples in each stack are consistently oriented with respect to machine direction (MD) and cross direction (CD). One of the stacks is designated for testing in the MD and the other for CD. Using a one inch precision cutter (Thwing Albert JDC-1-10, or similar) cut 4 MD strips from one stack, and 4 CD strips from the other, with dimensions of 1.00 in ±0.01 in wide by 3.0-4.0 in long. Each strip of one usable unit thick will be treated as a unitary specimen for testing.

Program the tensile tester to perform an extension test, collecting force and extension data at an acquisition rate of 20 Hz as the crosshead raises at a rate of 2.00 in/min (5.08 cm/min) until the specimen breaks. The break sensitivity is set to 80%, i.e., the test is terminated when the measured force drops to 20% of the maximum peak force, after which the crosshead is returned to its original position.

Set the gauge length to 1.00 inch. Zero the crosshead and load cell. Insert at least 1.0 in of the unitary specimen into the upper grip, aligning it vertically within the upper and lower jaws and close the upper grips. Insert the unitary specimen into the lower grips and close. The unitary specimen should be under enough tension to eliminate any slack, but less than 5.0 g of force on the load cell. Start the tensile tester and data collection. Repeat testing in like fashion for all four CD and four MD unitary specimens.

Program the software to calculate the following from the constructed force (g) verses extension (in) curve:

Tensile Strength is the maximum peak force (g) divided by the sample width (in) and reported as W/in to the nearest 1 W/in.

Adjusted Gauge Length is calculated as the extension measured at 3.0 g of force (in) added to the original gauge length (in).

Elongation is calculated as the extension at maximum peak force (in) divided by the Adjusted Gauge Length (in) multiplied by 100 and reported as % to the nearest 0.1%

Total Energy (TEA) is calculated as the area under the force curve integrated from zero extension to the extension at the maximum peak force (g*in), divided by the product of the adjusted Gauge Length (in) and specimen width (in) and is reported out to the nearest 1 g*in/in$^2$.

Replot the force (g) verses extension (in) curve as a force (g) verses strain curve. Strain is herein defined as the extension (in) divided by the Adjusted Gauge Length (in).

Program the software to calculate the following from the constructed force (g) verses strain curve:

Tangent Modulus is calculated as the slope of the linear line drawn between the two data points on the force (g) versus strain curve, where one of the data points used is the first data point recorded after 28 g force, and the other data point used is the first data point recorded after 48 g force. This slope is then divided by the specimen width (2.54 cm) and reported to the nearest 1 g/cm.

The Tensile Strength (g/in), Elongation (%), Total Energy (g*in/in$^2$) and Tangent Modulus (g/cm) are calculated for the four CD unitary specimens and the four MD unitary specimens. Calculate an average for each parameter separately for the CD and MD specimens.

Calculations:

Geometric Mean Tensile=Square Root of [MD Tensile Strength(g/in)×CD Tensile Strength(g/in)]

Geometric Mean Peak Elongation=Square Root of [MD Elongation(%)×CD Elongation (%)]

Geometric Mean TEA=Square Root of [MD TEA (g*in/in$^2$)×CD TEA(g*in/in$^2$)]

Geometric Mean Modulus=Square Root of [MD Modulus(g/cm)×CD Modulus(g/cm)]

Total Dry Tensile Strength(TDT)=MD Tensile Strength(g/in)+CD Tensile Strength(g/in)

Total TEA=MD TEA(g*in/in$^2$)+CD TEA(g*in/in$^2$)

Total Modulus=MD Modulus(g/cm)+CD Modulus(g/cm)

Tensile Ratio=MD Tensile Strength(g/in)/CD Tensile Strength(g/in)

Topographic Measurements of Differential Density Fibrous Substrates Test

Topographic measurements of differential density fibrous substrates are obtained via computer-controlled fringe-projection optical profilometry. Optical profilometer systems measure the physical dimensions of the test surface, resulting in a map of surface height elevation (z), versus lateral displacement in the x-y plane. A suitable optical profilometer instrument will have a field of view and x-y resolution such that the acquired images possess at least 10 pixels linearly across the narrowest feature being measured. A suitable instrument is a GFM Mikrocad system, running ODSCAD software version 4 or 6, or equivalent, available from GFMesstechnik GmbH, Teltow, Germany.

If necessary, in order to make samples suitably reflective for accurate measurement of the surface features, the surface to be measured is lightly sprayed with a very fine white powder spray. Preferably this spray is NORD-TEST Developer U 89, available from Helling GmbH, Heidgraben, Germany, which is sold for the detection of cracks in metal objects and welds. Samples should be equilibrated at 23° C.±2° C. and 50%±2% relative humidity for at least 2 hours immediately prior to applying such a spray, and for at least 2 hours after spraying. Care is taken to deposit only the minimum amount of white spray needed to create a thin reflective white coating.

Samples should be equilibrated at 23° C.±2° C. and 50%±2% relative humidity for at least 2 hours immediately prior to acquiring measurements.

The area of the fibrous substrates to be measured is restricted solely to areas possessing regions with different densities and excluding other areas or zones that might be present. The sample is placed with the surface area to be measured facing upward, underneath and normal to, the profilometer's projection head. The instrument manufacturer's instructions are followed, and optimized illumination and reflection requirements are achieved as outlined by the manufacturer. Digital images are then captured and stored.

Any portion of the image that is not part of the area to be measured should be cropped out of the captured image. Such cropping must occur prior to any further image processing, filtering or measurement analysis. The size of the resultant cropped image may vary between samples and images, depending upon the dimensions of the patterned area of that sample.

Figure 19:
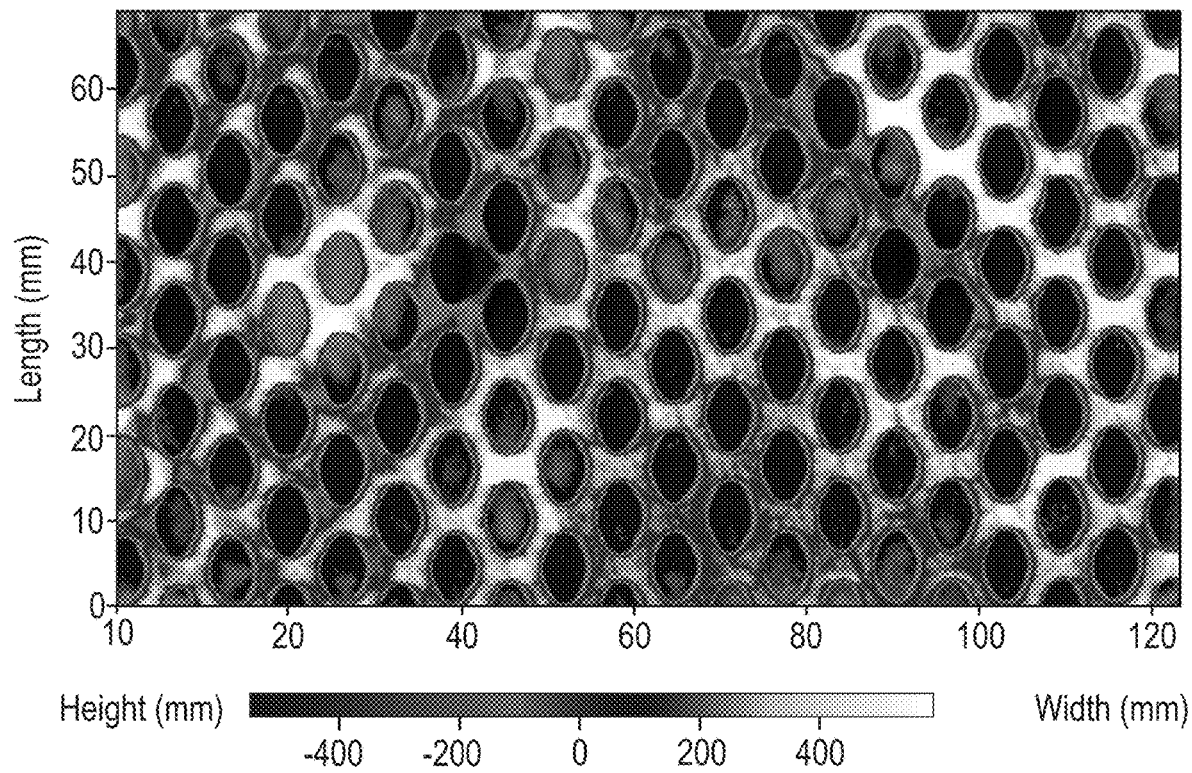
FIG. 19 is a processed topography image of a network region and a plurality of discrete zones of a fibrous substrate as shown using a SEM micrograph in accordance with the present disclosure.

Prior to making measurements, the images are processed in the instrument software, in order to lightly smooth noise in the images, and to reduce irregularity or waviness due to the sample's overall shape. This noise filtering processing includes the removal of invalid pixel values (those black pixels having a grey value at the dark limit of the grayscale range), and the removal of spike values or outlier peaks (those very bright pixels identified by the software as statistical outliers). A polynomial high-pass filter is then utilized with settings of: n=8, difference. For samples with very small features where it is difficult to clearly observe the pattern features, it may be useful to also apply a Fourier filter (for example: a 5 mm wave filter, fine structure result). When such a Fourier filter is used, it removes features larger than the filter length as noise, and consequently reduces variability, lowering the statistical standard deviation around the topography measurements. It is therefore essential that the size of the filter used is larger than any features of interest so as not to filter out said features. Processed images such as the topography image shown in FIG. 19, can be displayed, analyzed and measured. FIG. 19 was cropped then flattened via filtering with a polynomial (n=8 difference) filter to remove irregularity due to the sample's overall waviness.

Figure 20:
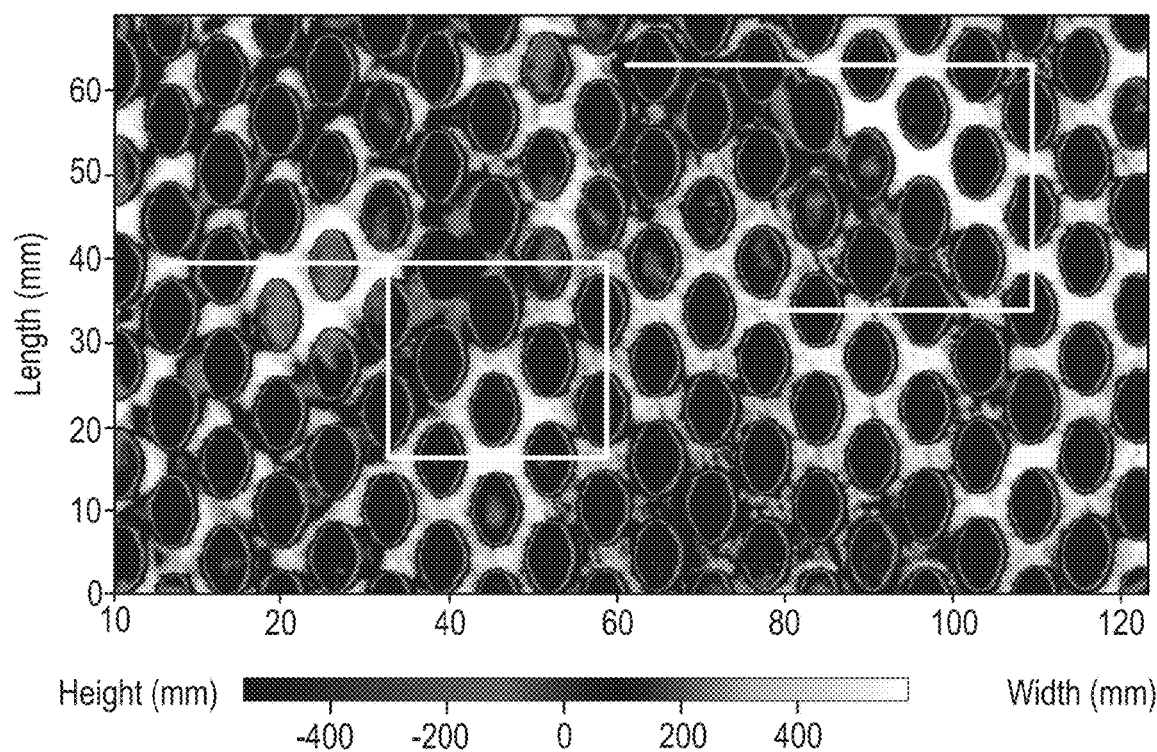
FIG. 20 illustrates a series of straight line regions of interest, drawn across the network region and discrete zones shown in FIG. 19. in accordance with the present disclosure.

Measurements are then made from the processed topography images to yield the spatial parameters of elevation differential (E), and transition region width (T). These measurements are achieved by using the instrument software to draw straight line regions of interest within a topography image of the sample's x-y surface, and to then generate height profile plots along these straight lines. The straight line regions of interest are drawn such that they sample several different locations within each image, crossing continuous regions and the center of adjacent discrete zones. The lines are drawn so that they bisect each transition region between continuous and discrete zones at an angle perpendicular to the long axis of the transition region, as shown in FIG. 20. As shown in FIG. 20, a series of straight line regions of interest, drawn across the continuous and discrete zones, bisecting each transition region at an angle perpendicular to the long axis of the transition region. The parameters (E) and (T) are then measured from the height profile plots generated from these straight line regions of interest.

Figure 21:
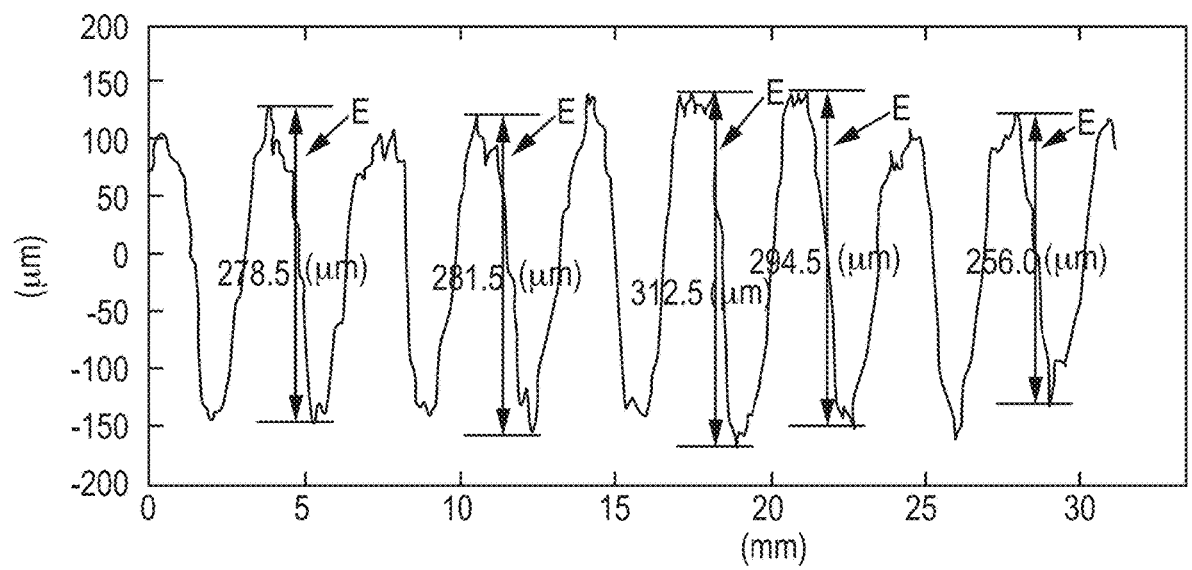
FIG. 21 illustrates a height profile plot along a straight line region of interest, drawn through a topography image, to show several elevation differential measurements in accordance with the present disclosure.
Figure 22:
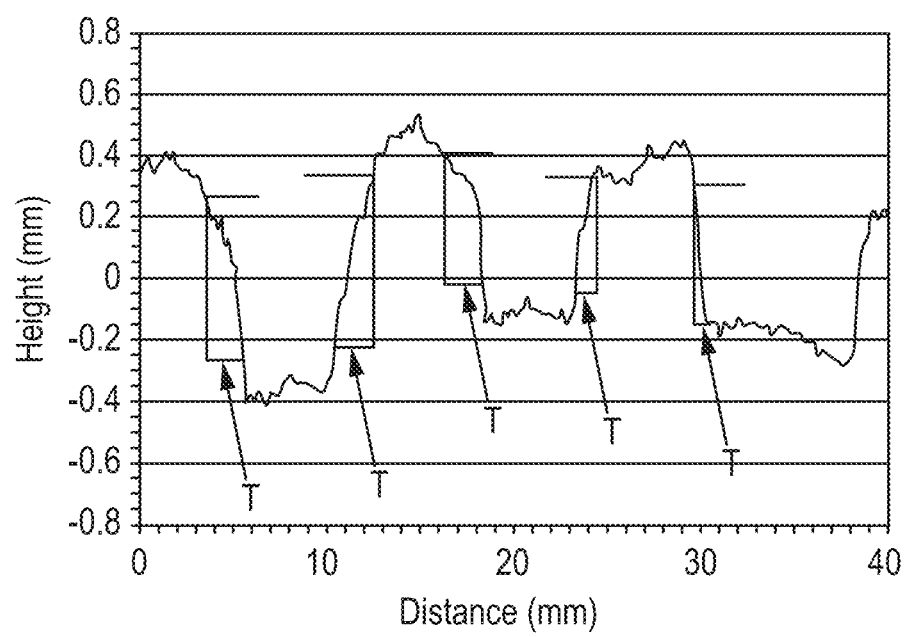
FIG. 22 depicts a height profile plot along a straight line region of interest, drawn through a topography image, to show several transition region widths in accordance with the present disclosure.

In a height profile plot, the plot's x-axis represents the length of the line, and the y-axis represents the vertical elevation of the surface perpendicular to the sample's planar surface. The elevation differential (E) is measured in micrometers as the vertical straight-line distance from the apex of a peak to the lowest point of an adjacent recess, on a height profile plot as shown in FIG. 21. As illustrated in FIG. 21, the height profile plot along a straight line region of interest, drawn through a topography image, shows several elevation differential (E) measurements. Typically this represents the maximum vertical elevation differential between the surface of a continuous region and an adjacent discrete zone, or vice versa. The transition region width (T) is measured in micrometers as the x-axis width of the curve across the central sixty percent (60%) of the elevation differential (E), on a height profile plot as shown in FIG. 22. As illustrated in FIG. 22, the height profile plot along a straight line region of interest, drawn through a topography image, shows several transition region widths (T). Typically, this represents the rate of transition from a continuous region to an adjacent discrete zone, or vice versa.

Where a sample has discrete zones which appear to fall into two or more distinct classes, as determined by visually observing their overall shape, size, elevation, and density, then separate values of (E) and (T) are to be determined for each discrete zone class and adjacent continuous region pairing.

If the sample visibly appears to have more than one pattern of discrete zones in different locations on the product, then each pattern is to have its values of (E) and (T) determined separately from the other pattern(s).

If a sample has a first region and an adjacent second region, wherein the first and second regions visibly appear to differ in their surface elevation, then the product is to have values of (E) and (T) measured from these regions. In this case all the method instructions given herein are to be followed and the first and second regions substituted for both the continuous region and the discrete zones named in this method.

For each pattern to be tested, five replicate product samples are imaged, and from each replicate sample measurements are made of at least ten elevation differentials (E) for each class of discrete zone, and ten transition region widths (T) for each class of discrete zone. This is repeated for each planar surface of each sample. Values of (E) and (T) are reported from the planar surface possessing the largest value of (E). For each parameter calculated for a specific pattern and discrete zone class, the values from each of the five replicate samples are averaged together to give the final value for each parameter.

Dry Caliper Test Method

The intent of this method is to provide a procedure to determine the dry caliper for each layer of the distribution material 54 under predefined pressure. The test can be executed with a conventional caliper micrometer, such as Type DM 2000 available from Wolf-Messtechnik GmbH, Am St. Niclas Schacht 13, Freiberg (Germany), having a circular sample foot of 15 mm diameter, having a weight for the foot of 17.2 g and additional weights of 20.0 g or 69.6 g or 106.9 g in order to achieve a total of 37.2 g or 86.8 g or 124.1 g to adjust the pressure to 2.065 kPa or 4.819 kPa or 6.889 kPa respectively (equivalent to 0.3 psi or 0.7 psi or 1.0 psi).

The caliper of each layer of the distribution material 54 is determined. The total caliper of the distribution material is the sum of the caliper of each layer of fibrous substrate of the distribution material.

The Dry Caliper measurement is carried out on the following square samples: of 3 cm centered on one single layer of the distribution material to obtain the caliper of one layer.

Basic Protocol for Dry Caliper

1. The distribution material is allowed to equilibrate at 23+−1 deg. C. and 50+−2% relative humidity for 8 hours.
2. The center of the sample is determined as described above and marked on the wearer surface of the sample.
3. The sample is positioned under the caliper gauge with the wearer surface toward the sample contact foot and with the center of the sample centered under the foot.
5. The sample contact foot is gently lowered into contact with the surface of the sample.
6. A Pressure of 2.06 kPa (0,3 psi) or 4.819 kPa (0.7 psi) or 6.889 kPa (1.0 psi) is applied.
7. The caliper reading is taken 2 seconds after the foot comes into contact with the sample.

The caliper is the average of three replicates and is reported in millimeters rounded to the nearest 0.01 mm.

In-Bag Stack Height Test

The in-bag stack height of a package of the absorbent articles of the present disclosure is determined as follows:

Equipment

Universal Diaper Packaging Tester (UDPT) (Model #M-ROEL; Machine #MK-1071), including a horizontal sliding plate (horizontal plate that moves up and down in a vertical plane) for adding weights. It is counter-balanced by a suspended weight to assure that no downward force is added from the horizontal sliding plate assembly to the diaper package at all times. The UDPT is available from Matsushita Industry Co. LTD, 7-21-101, Midorigaoka-cho, Ashiya-city, Hyogo JAPAN. Zip code: 659-0014. A 850 g (+1−0.5 g) weight.

DEFINITIONS

Figure 23:
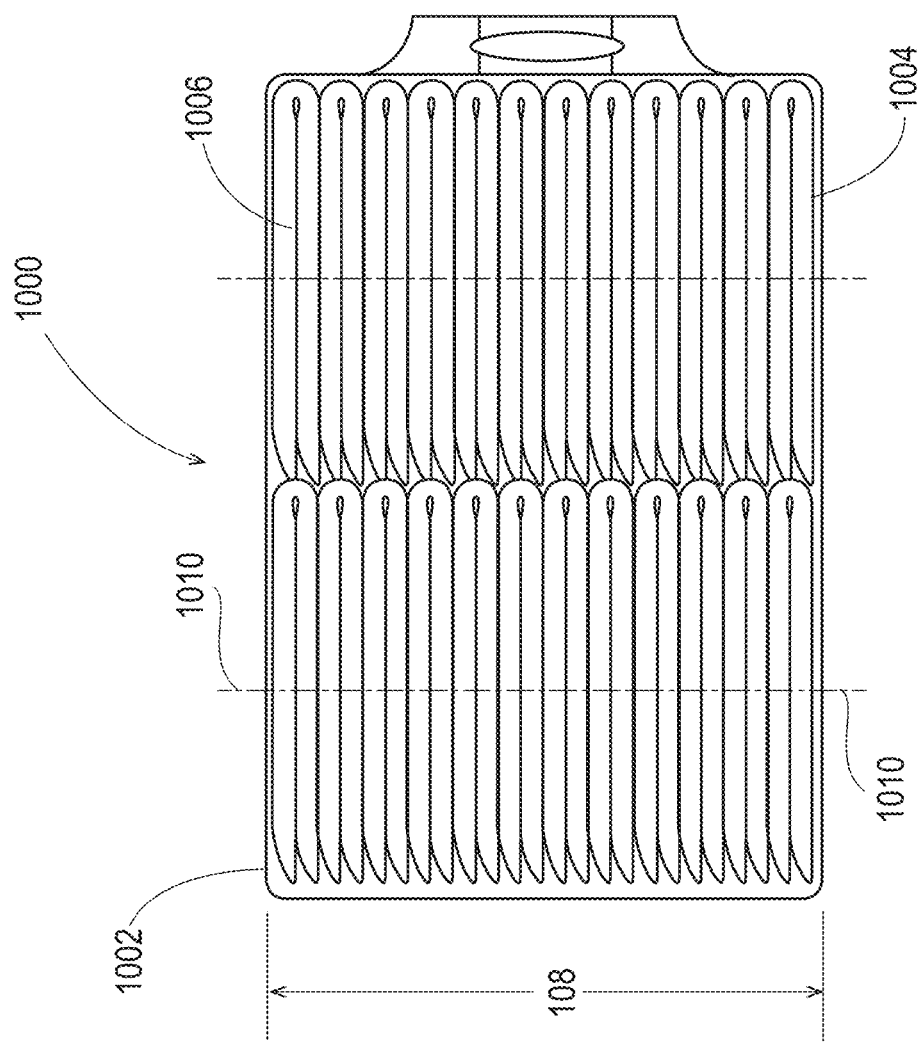
FIG. 23 is a side view of a package of absorbent articles showing the package width. The outer surface is illustrated as transparent for purposes of clarity.

As illustrated in FIG. 23, a package 1000 defines an interior space 1002 and comprises a plurality of absorbent articles 1004. The absorbent articles are in a stack 1006. The package has a package width 1008. The package width 1008 is defined as the maximum distance between the two highest bulging points along the same compression stack axis 1100 of the absorbent article package 1000.

In-Bag Stack Height=(Package Width/Pad Count Per Stack)×10 absorbent articles.

Apparatus Calibration

Pull down the horizontal sliding plate until its bottom touches the tester base plate.

Set the digital meter located at the side of the horizontal sliding scale to zero mark.

Raise the horizontal sliding plate away from the tester base plate.

Test Procedure

Put one of the side panel of the absorbent article package along its width standing at the center of the tester base plate. Make sure the vertical sliding plate (vertical plate that moves left and right in a horizontal plane) is pulled to the right so it does not touch the package being tested.

Add the 850 g weight onto the vertical sliding plate.

Allow the horizontal sliding plate to slide down slowly until its bottom lightly touches desired highest point of the package.

Measure the package width in mm (distance from the top of the base plate to the top of the diaper package).

Record the reading that appears on the digital meter.

Remove the 850 g weight.

Raise the horizontal sliding plate away from the diaper package.

Remove the absorbent article package.

Calculation/Reporting

Calculate and report the "In-Bag Stack Height"= (Package Width/Pad Count Per Stack)×10.

Report Sample Identification, i.e. complete description of product being tested (product brand name/size).

Report the determined value for each width measurement to the nearest 1 mm. At least five absorbent article packages having the same pad count are measured in this manner for a given product and the in-bag stack height values are aggregated to calculate an average and standard deviation.

Report the Production Date of the measured package (taken from package coding).

Report the Testing Date and Analytical Method used.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any embodiment disclosed or claimed herein or that it alone, or in any combination with any other reference or references, teaches, suggests or discloses any such embodiment. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications may be made without departing from the spirit and scope of the present disclosure.

It is therefore intended to cover in the appended claims all such changes and modifications that are within the scope of this disclosure.

What is claimed is:

1. An absorbent article, comprising:
   a central longitudinal axis;
   a liquid permeable topsheet;
   a liquid impermeable backsheet;
   an absorbent core positioned at least partially intermediate the topsheet and the backsheet, wherein the absorbent core comprises an absorbent material positioned within a core wrap, wherein the core wrap forms a C-wrap, and wherein the absorbent material comprises a substantially absorbent material free area surrounded on all sides by the absorbent material;
   a distribution material positioned intermediate the topsheet and the core wrap and comprising two or more substrates, wherein a plurality of the two or more substrates comprise wet-laid, three-dimensional fibrous substrates comprising at least 80% pulp fibers by weight of the three-dimensional fibrous substrates, wherein the plurality of the three-dimensional fibrous substrates each comprise:
      a continuous network region, wherein the continuous network region comprises a first average density; and
      a plurality of discrete zones comprising a second average density, wherein the discrete zones are dispersed throughout the continuous network region, and wherein the first average density and the second average density are different;
   an acquisition material positioned intermediate the topsheet and the distribution material; and
   at least one of the two or more substrates is formed by folding the at least one substrate fully over itself, wherein the at least one substrate forms a dual layer at least in an area that overlaps the central longitudinal axis of the absorbent article.

2. The absorbent article of claim 1, wherein the wet-laid, three-dimensional fibrous substrates are creped, and wherein the three-dimensional aspects of the three-dimensional fibrous substrates are wet-formed.

3. The absorbent article of claim 1, wherein the wet-laid, three-dimensional fibrous substrates comprise at least 90% pulp fibers by weight of the wet-laid, three-dimensional fibrous substrates.

4. The absorbent article of claim 1, wherein the wet-laid, three-dimensional fibrous substrates comprise discrete embossments.

5. The absorbent article of claim 1, wherein the absorbent material comprises at least 85% of superabsorbent polymers, by total weight of the absorbent material.

6. The absorbent article of claim 5, wherein the absorbent core comprises an adhesive configured to aid in immobilizing the absorbent material.

7. The absorbent article of claim 1, wherein the absorbent material comprises at least 95% of superabsorbent polymers, by total weight of the absorbent material.

8. The absorbent article of claim 1, wherein the substantially absorbent material free area defines an arcuate shape.

9. The absorbent article of claim 1, wherein the wet-laid, three-dimensional fibrous substrates are uncreped.

10. The absorbent article of claim 1, comprising:
    leg cuffs; and
    a waist edge.

11. The absorbent article of claim 1, comprising:
    a front region;
    a crotch region; and
    a rear region, wherein the crotch region is positioned intermediate the front region and the rear region, wherein the distribution material has a first profile in the front region, the crotch region, or the rear region, and wherein the distribution material has a second, different profile in another of the regions.

12. The absorbent article of claim 1, wherein the absorbent article is a sanitary napkin.

13. The absorbent article of claim 1, wherein the wet-laid, three-dimensional fibrous substrates have a Geometric Mean TEA of about 100 g*in/in$^2$ to about 500 g*in/in$^2$, according to the Tensile Test herein.

14. The absorbent article of claim 1, wherein the wet-laid, three-dimensional fibrous substrates have a Geometric Mean Tensile of about 700 g/in to about 1,100 g/in, according to the Tensile Test herein.

15. The absorbent article of claim 1, wherein the wet-laid, three-dimensional fibrous substrates have a Geometric Mean Modulus of about 1,000 g/cm to about 3,000 g/cm, according to the Tensile Test herein.

16. The absorbent article of claim 1, wherein the wet-laid, three-dimensional fibrous substrates have a Geometric Mean Peak Elongation of about 10% to about 23%, according to the Tensile Test herein.

17. The absorbent article of claim 1, wherein the wet-laid, three-dimensional fibrous substrates have a Wet Burst Strength of about 50 g to about 500 g, according to the Wet Burst Strength Test herein.

18. A package comprising a plurality of the absorbent articles of claim 1, wherein the package has an in-bag stack height of less than about 80 mm, according to the In-Bag Stack Height Test herein.

19. An absorbent article, comprising:
    a central longitudinal axis;
    a liquid permeable topsheet;
    a liquid impermeable backsheet;
    an absorbent core positioned at least partially intermediate the topsheet and the backsheet, wherein the absorbent core comprises an absorbent material positioned within a core wrap, wherein the core wrap forms a C-wrap, and wherein the absorbent material comprises a substantially absorbent material free area surrounded on all sides by the absorbent material;
    a distribution material positioned intermediate the topsheet and the core wrap and comprising two or more substrates, wherein a plurality of the two or more substrates comprise wet-formed, three-dimensional fibrous substrates comprising at least 80% pulp fibers by weight of the wet-formed, three-dimensional fibrous substrates, wherein the plurality of the wet-formed, three-dimensional fibrous substrates each comprise:
       a wet strength resin;
       a continuous network region, wherein the continuous network region comprises a first average density; and
       a plurality of discrete zones comprising a second average density, wherein the discrete zones are dispersed throughout the continuous network region, and wherein the first average density is different than the second average density;
    an acquisition material positioned intermediate the topsheet and the distribution material; and
    at least one substrate of the two or more substrates is fully folded over itself to form a two layer structure that overlaps the central longitudinal axis.

20. The absorbent article of claim 19 wherein the wet-formed, three-dimensional fibrous substrates are creped, wherein the continuous network region has a first basis weight, wherein the plurality of discrete zones have a second basis weight, wherein the first and second basis weights are different, wherein the continuous network region has a first dry caliper, wherein the plurality of discrete zones have a second dry caliper, and wherein the first and second dry calipers are different.

21. A package comprising:
a plurality of absorbent articles, wherein each of the absorbent articles comprises:
  a central longitudinal axis;
  a liquid permeable topsheet;
  a liquid impermeable backsheet;
  an absorbent core positioned at least partially intermediate the topsheet and the backsheet, wherein the absorbent core comprises an absorbent material comprising at least 80% superabsorbent polymers by weight of the absorbent material, wherein the absorbent material is positioned within a core wrap, wherein the core wrap forms a C-wrap, wherein the absorbent material comprises a substantially absorbent material free area surrounded on all sides by the absorbent material, and wherein the substantially absorbent material free area defines an arcuate shape;
  a distribution material positioned intermediate the topsheet and the core wrap and comprising two or more substrates, wherein a plurality of the two or more substrates comprise wet-formed, three-dimensional fibrous substrates comprising at least 80% pulp fibers by weight of the wet-formed, three-dimensional fibrous substrates, wherein the plurality of the wet-formed, three-dimensional fibrous substrates each comprise:
    a wet strength resin;
    a continuous network region, wherein the continuous network region comprises a first average density; and
    a plurality of discrete zones comprising a second average density, wherein the discrete zones are dispersed throughout the continuous network region, wherein the first average density is different than the second average density;
an acquisition material positioned intermediate the topsheet and the distribution material; and
wherein the package has an in-bag stack height of less than about 80 mm, according to the In-Bag Stack Height Test herein; and
at least one substrate of the two or more substrates is fully folded over itself to form a two layer structure that overlaps the central longitudinal axis.

* * * * *